United States Patent
Tsusaka et al.

(10) Patent No.: US 9,233,467 B2
(45) Date of Patent: Jan. 12, 2016

(54) CONTROL APPARATUS AND METHOD FOR MASTER-SLAVE ROBOT, MASTER-SLAVE ROBOT, AND CONTROL PROGRAM

(71) Applicant: Panasonic Intellectual Property Management Co., Ltd., Osaka (JP)

(72) Inventors: Yuko Tsusaka, Osaka (JP); Yudai Fudaba, Osaka (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 67 days.

(21) Appl. No.: 14/071,994

(22) Filed: Nov. 5, 2013

(65) Prior Publication Data
US 2014/0195052 A1    Jul. 10, 2014

(30) Foreign Application Priority Data
Jan. 10, 2013  (JP) .................................. 2013-002687

(51) Int. Cl.
G05B 19/04 (2006.01)
G05B 19/18 (2006.01)
(Continued)

(52) U.S. Cl.
CPC ............ *B25J 9/1633* (2013.01); *A61B 19/2203* (2013.01); *B25J 3/04* (2013.01); *B25J 9/1689* (2013.01); *A61B 2019/2223* (2013.01); *A61B 2019/2292* (2013.01); *A61B 2019/2296* (2013.01); *A61B 2019/464* (2013.01); *G05B 2219/40138* (2013.01)

(58) Field of Classification Search
CPC ....... B25J 9/1689; B25J 9/0084; B25J 9/1633
USPC .......... 700/245, 257, 258, 260, 264; 901/1, 2, 901/6
See application file for complete search history.

(56) References Cited

U.S. PATENT DOCUMENTS

| | | | | |
|---|---|---|---|---|
| 5,266,875 A | * | 11/1993 | Slotine | B25J 9/1689 318/568.1 |
| 5,389,865 A | * | 2/1995 | Jacobus | B25J 9/1689 318/568.1 |

(Continued)

FOREIGN PATENT DOCUMENTS

| | | |
|---|---|---|
| JP | 08-164807 | 6/1996 |
| JP | 2011-517419 | 6/2011 |
| WO | 2012/029227 | 3/2012 |

*Primary Examiner* — Khoi Tran
*Assistant Examiner* — Jorge Peche
(74) *Attorney, Agent, or Firm* — Wenderoth, Lind & Ponack, L.L.P.

(57) ABSTRACT

A master-slave device grips an object and performs a task while being in contact with a to-be-treated object. A force detection unit measures force information given to a slave mechanism. A force correction determination unit determines a force correction part serving as information from correction start to end times of force information transmitted to a master mechanism and, as a correcting method to perform correction, a first method determining a gain such that a reduction in absolute value of force information at the force correction part is maintained for a predetermined period of time or a second method determining a gain such that a reduction and an increase in the absolute value are repeated within a range that is not more than a value by reducing the absolute value. A force correction unit corrects information of a type of a force based on the force correction part and the gain.

10 Claims, 22 Drawing Sheets

(51) Int. Cl.
*B25J 9/16* (2006.01)
*A61B 19/00* (2006.01)
*B25J 3/04* (2006.01)

(56) References Cited

U.S. PATENT DOCUMENTS

| | | | | |
|---|---|---|---|---|
| 6,801,008 B1* | 10/2004 | Jacobus | ............... | B25J 9/1689 318/560 |
| 7,819,859 B2* | 10/2010 | Prisco | ............... | A61B 19/22 345/156 |
| 7,865,266 B2* | 1/2011 | Moll | ............... | A61B 19/2203 414/1 |
| 2003/0114962 A1* | 6/2003 | Niemeyer | ............... | A61B 19/22 700/245 |
| 2005/0200324 A1* | 9/2005 | Guthart | ............... | A61B 19/22 318/568.11 |
| 2005/0202384 A1* | 9/2005 | DiCuccio | ............... | G09B 23/285 434/262 |
| 2006/0241414 A1* | 10/2006 | Nowlin | ............... | A61B 19/22 600/431 |
| 2007/0112466 A1* | 5/2007 | Ohnishi | ............... | G05B 19/19 700/260 |
| 2009/0088774 A1* | 4/2009 | Swarup | ............... | A61B 19/2203 606/130 |
| 2009/0216374 A1* | 8/2009 | Low | ............... | B25J 9/1689 700/258 |
| 2009/0248038 A1 | 10/2009 | Blumenkranz et al. | | |
| 2010/0139436 A1* | 6/2010 | Kawashima | ............... | B25J 17/0266 74/490.01 |
| 2011/0105898 A1* | 5/2011 | Guthart | ............... | A61B 19/22 600/437 |
| 2012/0071752 A1* | 3/2012 | Sewell | ............... | A61B 6/12 600/424 |
| 2012/0191245 A1* | 7/2012 | Fudaba | ............... | B25J 9/1633 700/254 |
| 2013/0116706 A1* | 5/2013 | Lee | ............... | A61B 19/2203 606/130 |

* cited by examiner

Fig.6

| TIME (msec) | FORCE (N,Nm) | POSITION (m) | BASING POINT | ID |
|---|---|---|---|---|
| $t_0$ | $f_0$ | $p_0$ | 1 | 1 |
| $t_{01}$ | $f_{01}$ | $p_{01}$ | 0 | 1 |
| .. | .. | .. | .. | .. |
| $t_1$ | $f_1$ | $p_1$ | 1 | 2 |
| $t_{11}$ | $f_{11}$ | $p_{11}$ | 0 | 2 |
| .. | .. | .. | .. | .. |
| $t_2$ | $f_2$ | $p_2$ | 1 | 3 |
| $t_{21}$ | $f_{21}$ | $p_{21}$ | 0 | 3 |
| ⋮ | ⋮ | ⋮ | ⋮ | ⋮ |

Fig.7

| TIME (msec) | FORCE (N,Nm) | POSITION (m) | ID OF REFERENCE INFORMATION | INDIVIDUAL FORCE |
|---|---|---|---|---|
| $t_0$ | $f_0$ | $p_0$ | 1 | $fr_0$ |
| $t_{01}$ | $f_{01}$ | $p_{01}$ | 1 | $fr_{01}$ |
| .. | .. | .. | .. | .. |
| $t_1$ | $f_1$ | $p_1$ | 20 | $fr_1$ |
| $t_{11}$ | $f_{11}$ | $p_{11}$ | 20 | $fr_{11}$ |
| .. | .. | .. | .. | .. |
| $t_2$ | $f_2$ | $p_2$ | 1 | $fr_2$ |
| $t_{21}$ | $f_{21}$ | $p_{21}$ | 1 | $fr_{21}$ |
| ⋮ | ⋮ | ⋮ | ⋮ | ⋮ |

*Fig.16H*
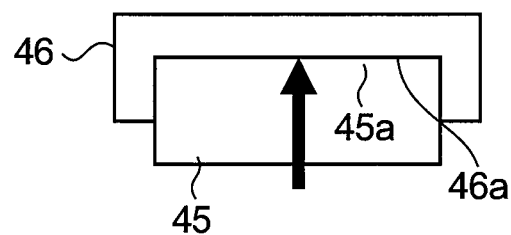
*Fig.17*
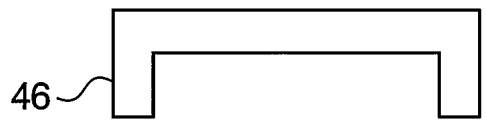
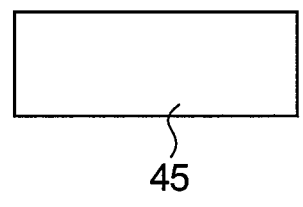
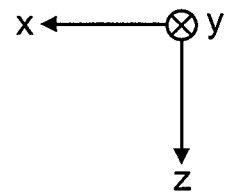

CONTROL APPARATUS AND METHOD FOR MASTER-SLAVE ROBOT, MASTER-SLAVE ROBOT, AND CONTROL PROGRAM

BACKGROUND OF THE INVENTION

The technical field relates to a control apparatus and method for a master-slave robot to generate or teach an operation of, for example, a robot arm master-slave robot, a master-slave robot having a control apparatus for a master-slave robot, and a control program for a master-slave robot. The present invention relates to a force measurement device in a manipulation by a person, a control apparatus and method for a master-slave robot that assists a manipulation by a person, a master-slave robot, and a control program.

In recent years, there is a master-slave robot in which a master robot is remotely manipulated by a person to cause a slave robot to perform a task.

For example, endoscopic surgery is performed such that an operator fits a tube called a trocar in a hole formed in the abdomen of a human body, inserts a tip end of a surgical instrument such as a dedicated endoscope or a forceps fixed to a slave from the trocar into the body, and manipulates a master while watching a video image of the endoscope displayed on a monitor screen to move the forceps fixed to the slave by remote control from the master. Even though a special doctor is not at the site, a surgical operation can be performed through the remote operation.

At a manufacturing premise, there is proposed a master-slave robot that remotely teaches a slave in an overseas factory from a domestic factory. In particular, regardless of location, a skilled task such as a flexible substrate insertion task can be taught such that a skilled person in the domestic factory remotely teaches a slave machine in an overseas factory.

In any master-slave system, in addition to a function of manipulating a master to smoothly manipulate a slave, a function of feeding back a force acting on the slave to the master is required.

However, in feeding back a force acting on the slave to the master, when the master and the slave have different inertia forces (for example, a slave is heavy and a master is light) and the force acting on the slave is fed back to the master, the inertia force in addition to the force is applied to the master. For this reason, large force is applied to the master, which causes large movement of the master. When the master largely moves, the slave also largely moves, and, by a work such as a flexible substrate gripped with the slave, a forceps gripped with an operator or the slave may hurt a living body.

As a method of feeding back a force acting on the slave to the master, force sensors are disposed on an arm portion of a surgical robot and a surgical instrument, and a force acting on a tip end of a forceps or a force acting on a robot arm is detected to feed back the force to the operator (see Patent Literature 1 (Japanese Translation of PCT Publication No. 2011-517419)).

As a proposal of feeding back a force acting on a slave to a master, there is a proposal that a force acting on the tip end of the slave is detected, and, when an impulse calculated from the detected force is a predetermined threshold value or more, the magnitude of a force fed back to the master is corrected to be decreased (see Patent Literature 2 (Japanese Unexamined Patent Publication No. 8-164807)).

In addition, there is a proposal that, based on information of a force acting on the slave or a velocity thereof, the force acting on the slave is enlarged to fed back to the master (see Patent Literature 3 (WO 2012/029227)).

SUMMARY OF THE INVENTION

However, in Patent Literature 1, although the force acting on the slave can be fed back to the master, in a case where inertia forces of the slave and the master are different from each other, when the force acting on the slave is fed back to the master, the inertia force in addition to the force acting on the slave is applied to the master. For this reason, large force is applied to the master, which causes large movement of the master.

In Patent Literature 2 and Patent Literature 3, since the force acting on the slave can be corrected and fed back to the master machine, even though the slave and the master have different inertia forces, the master can be prevented from being largely moved due to application of large force to the master. However, in contrast to this, since the force acting on the master machine is corrected to be decreased and then fed back, a problem in which a person cannot easily feel the force that is fed back is posed.

One non-limiting and exemplary embodiment provides a control apparatus and method for a master-slave robot; a master-slave robot; and a control program, in each of which, even though a slave mechanism and a master mechanism have different inertia forces, the master mechanism can be prevented from being largely moved due to application of large force to the master mechanism, and, even though correction is performed to prevent the master mechanism from being largely moved, a person can feel a fed-back force.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: A control apparatus for a master-slave robot comprising a slave mechanism that grips an object and performs a task while being in contact with an object to be treated and a master mechanism that causes a person to remotely-manipulate the slave mechanism, the control apparatus comprising:

a force information acquiring unit that acquires force information of an external force acting on the slave mechanism;

a force correction determination unit that, based on at least one piece of information of the force information and velocity information of the slave mechanism, determines a force correction part serving as information of a section from a correction start time serving as start time of correction of the force information to a correction end time serving as end time of the correction and, as a correcting method, any one of two methods including a first method that determines a gain such that a reduction in an absolute value of the force information of the force correction part at the force correction part is maintained for a predetermined period of time to perform correction and a second method that determines a gain such that a reduction and an increase in the absolute value of the force information of the force correction part at the force correction part are repeated within a range that is not more than a value obtained by reducing the absolute value, to perform correction;

a force correction unit that corrects the force information acquired by the force information acquiring unit by the correcting method determined by the force correction determination unit based on the correction part and the gain that are determined by the force correction determination unit;

a force transmitting unit that transmits, to the master mechanism, force information after the correction is performed by the force correction unit;

a master control unit that controls manipulation information of the master mechanism when the person manipulates a master manipulator based on the corrected force information transmitted from the force transmitting unit; and a slave control unit that is connected to the slave mechanism and the master control unit and outputs a control signal that transmits the manipulation information of the master mechanism sent from the master control unit to the slave mechanism.

These general and specific aspects may be implemented using a system, a method, and a computer program, and any combination of systems, methods, and computer programs.

According to the control apparatus and method for a master-slave robot, a master slave robot, and a control program of the above aspect of the present invention, even though the slave mechanism and the master mechanism have different inertia forces, the master mechanism can be prevented from being largely moved due to application of large force to the master mechanism, and, even though the correction is performed to prevent the master mechanism from being largely moved, the person can feel a fed-back force.

BRIEF DESCRIPTION OF THE DRAWINGS

These and other aspects and features of the present disclosure will become clear from the following description taken in conjunction with the embodiments thereof with reference to the accompanying drawings, in which:

FIG. 6 is a view of a reference information database according to the first embodiment of the present invention;

FIG. 7 is a view of a measurement information database according to the first embodiment of the present invention;

FIG. 16H is a plan view of the periphery of the flexible substrate insertion hole, describing the manipulation of flexible substrate insertion, corresponding to FIG. 16D, in the second embodiment of the present invention;

FIG. 17 is a view for describing a coordinate system of flexible substrate insertion task in the second embodiment of the present invention;

DETAILED DESCRIPTION OF THE EMBODIMENTS

Figure 1:
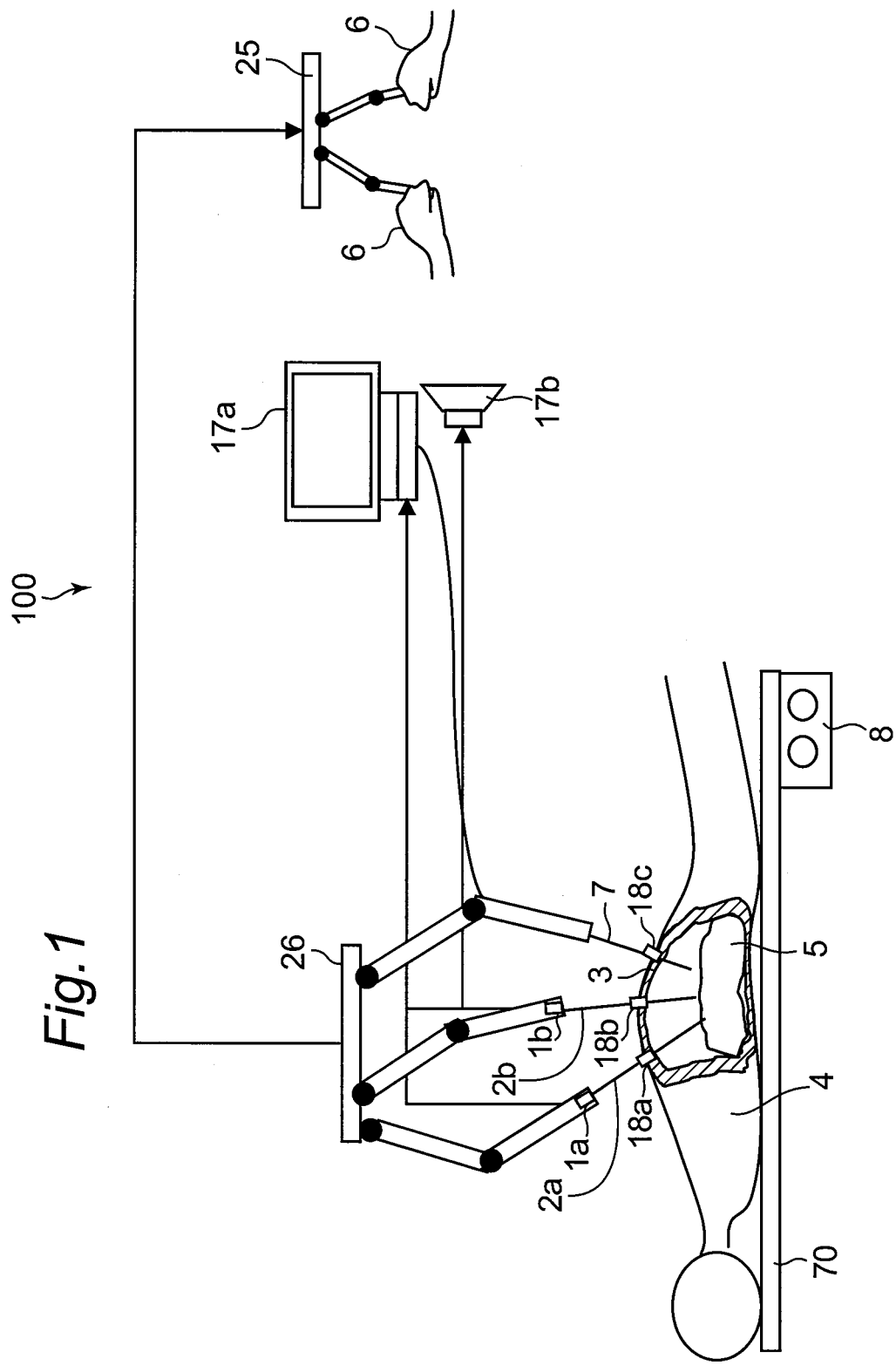
FIG. 1 is a view showing an outline of a configuration of a master-slave device according to a first embodiment of the present invention.

Embodiments of the present invention will be described below with reference to the drawings.

Various aspects of the present invention will be described below before the embodiments of the present invention will be described in detail with reference to the drawings.

Examples of the disclosed technique are as follows.

1st aspect: A control apparatus for a master-slave robot comprising a slave mechanism that grips an object and performs a task while being in contact with an object to be treated and a master mechanism that causes a person to remotely-manipulate the slave mechanism, the control apparatus comprising:

a force information acquiring unit that acquires force information of an external force acting on the slave mechanism;

a force correction determination unit that, based on at least one piece of information of the force information and velocity information of the slave mechanism, determines a force correction part serving as information of a section from a correction start time serving as start time of correction of the force information to a correction end time serving as end time of the correction and, as a correcting method, any one of two methods including a first method that determines a gain such that a reduction in an absolute value of the force information of the force correction part at the force correction part is maintained for a predetermined period of time to perform correction and a second method that determines a gain such that a reduction and an increase in the absolute value of the force information of the force correction part at the force correction part are repeated within a range that is not more than a value obtained by reducing the absolute value, to perform correction;

a force correction unit that corrects the force information acquired by the force information acquiring unit by the correcting method determined by the force correction determination unit based on the correction part and the gain that are determined by the force correction determination unit;

a force transmitting unit that transmits, to the master mechanism, force information after the correction is performed by the force correction unit;

a master control unit that controls manipulation information of the master mechanism when the person manipulates a master manipulator based on the corrected force information transmitted from the force transmitting unit; and a slave control unit that is connected to the slave mechanism and the master control unit and outputs a control signal that transmits the manipulation information of the master mechanism sent from the master control unit to the slave mechanism.

With this configuration, even though the slave mechanism and the master mechanism have different inertia forces, the master mechanism can be prevented from being largely moved due to application of large force to the master mechanism, and, even though the correction is performed to prevent the master mechanism from being largely moved, the person can feel a fed-back force.

2nd aspect: The control apparatus for a master-slave robot according to the 1st aspect, wherein the force correction determination unit determines as the correcting method, any one of three method including the first and second methods and a third method that determines a gain to reduce the absolute value of the force information of the force correction part after a predetermined period of time has elapsed, to perform correction.

With the configuration, no-feedback time is elongated before a force is fed back, to make it possible to make the person easily feel a force during a task.

3rd aspect: The control apparatus for a master-slave robot according to the 1st or 2nd aspect, wherein the force information acquiring unit includes:

a force detection unit that detects information of the force obtained when the object is brought into contact with the object to be treated;

a reference information generating unit that generates reference information serving as information relating to the force in the object being not in contact with the object to be treated; and an individual force calculating unit that individually calculates a force generated when the object acts on the object to be treated based on the information of the force acquired by the force detection unit and the reference information when the object is brought into contact with the object to be treated, and the force correction determination unit determines the force correction part and determines whether a force to be corrected by the force correction unit is of a type of the information of the force acquired by the force information acquiring unit or a type of a force individually acting on the object to be treated by the object.

With the configuration, forces individually acting on an object to be treated can be calculated (estimated) based on a measured force.

4th aspect: The control apparatus for a master-slave robot according to any one of the 1st to 3rd aspects, wherein the force correction determination unit determines a correction amount set when the absolute value of the force information at the force correction part is reduced, based on at least one piece of information of a type of one of the force acquired by the force information acquiring unit and the force individually acting on the object to be treated by the object and information of a degree of flexibility of the object or the object to be treated.

With the configuration, even though the slave mechanism and the master mechanism have different inertia forces, the master mechanism can be prevented from being largely moved due to application of large force to the master mechanism, and a method for performing correction to prevent the master mechanism from being largely moved in consideration of the type of the force or the degree of flexibility can be appropriately determined.

5th aspect: The control apparatus for a master-slave robot according to the 4th aspect, wherein the force correction determination unit determines a correction amount such that the correction amount decreases with an increased degree of flexibility of the object or the object to be treated in a plurality of directions including a task direction and a direction intersecting with the task direction.

With the configuration, even though the slave mechanism and the master mechanism have different inertia forces, the master mechanism can be prevented from being largely moved due to application of large force to the master mechanism, and a method for performing correction to prevent the master mechanism from being largely moved in consideration of a task direction or the like can be appropriately determined.

6th aspect: The control apparatus for a master-slave robot according to the 4th aspect, wherein the force correction determination unit determines correction such that a correction amount set when the type of the force determined by the force correction determination unit is determined as the force individually acting on the object to be treated by the object is larger than a correction amount determined as the information of the force acquired by the force information acquiring unit.

With the configuration, even though the slave mechanism and the master mechanism have different inertia forces, the master mechanism can be prevented from being largely moved due to application of large force to the master mechanism, and a method for performing correction to prevent the master mechanism from being largely moved in consideration of a difference between correction amounts that vary depending on types of forces can be appropriately determined.

7th aspect: The control apparatus for a master-slave robot according to the 1st or 4th aspect, wherein the force correction determination unit selects a method that determines such a gain that an absolute value of force information at the force correction part is reduced by a predetermined correction amount to perform correction, when the correction amount is smaller than a threshold value for determining a predetermined correcting method, and determines the first method or the second method when the correction amount is not less than the threshold value for determining a predetermined correcting method.

With the configuration, even though the slave mechanism and the master mechanism have different inertia forces, the master mechanism can be prevented from being largely moved due to application of large force to the master mechanism, and a method for performing correction to prevent the master mechanism from being largely moved in consideration of the correction amount can be appropriately determined.

8th aspect: The control apparatus for a master-slave robot according to the 3rd aspect, comprising a force decision unit that decides that a load is applied to the object or the object to be treated, when information of the force detected by the reference information generating unit or the individual force calculated by the individual force calculation unit is not less than a predetermined threshold value for deciding load.

With the configuration, the force decision unit can automatically decide whether the load is applied to the object or the object to be treated.

9th aspect: The control apparatus for a master-slave robot according to any one of the 2nd to 8th aspects, further comprising a decision result notification unit that adds a force calculated by the reference information generating unit or an individual force calculated by the individual force calculating unit or a decision result decided by the force decision unit to an image obtained by imaging the object or the object to be treated to display a resultant image.

With the configuration, when a load is applied to the object or the object to be treated, the person can check a situation of the load together with a taken image through the decision result notification unit.

10th aspect: The control apparatus for a master-slave robot according to any one of the 2nd to 8th aspects, further comprising a decision result notification unit that notifies, by voice, the person of the force calculated by the reference information generating unit or the individual force calculated by the individual force calculation unit or a decision result decided by the force decision unit.

With the configuration, when the load is applied to the object or the object to be treated, the person can be notified by voice through the decision result notification unit.

11th aspect: A master-slave robot comprising:

the control apparatus for a master-slave robot according to any one of the 1st to 9th aspects; and the master-slave device.

With the configuration, even though the slave mechanism and the master mechanism have different inertia forces, the master mechanism can be prevented from being largely moved due to application of large force to the master mechanism, and, even though correction is performed to prevent the master mechanism from being largely moved, the person can feel a fed-back force.

12th aspect: A method of controlling a master-slave robot that controls a master-slave device comprising a slave mechanism that grips an object and performs a task while being in contact with an object to be treated and a master mechanism that causes a person to remotely-manipulate the slave mechanism, the method comprising:

causing a force information acquiring unit to acquire force information of an external force acting on the slave mechanism;

causing a force correction determination unit, based on at least one piece of information of the force information and velocity information of the slave mechanism, to determine a force correction part serving as information of a section from a correction start time serving as start time of correction of the force information to a correction end time serving as end time of the correction and, as a correcting method, any one of two methods including a first method that determines a gain such that a reduction in an absolute value of the force information of the force correction part at the force correction part is maintained for a predetermined period of time to perform correction and a second method that determines a gain such that a reduction and an increase in the absolute value of the force information of the force correction part at the force correction part are repeated within a range that is not more than a value obtained by reducing the absolute value, to perform correction;

causing a force correction unit to correct the force information acquired by the force information acquiring unit by the correcting method determined by the force correction determination unit based on the correction part and the gain that are determined by the force correction determination unit;

causing a force transmitting unit to transmit, to the master mechanism, force information after the correction is performed by the force correction unit;

causing a master control unit to control manipulation information of the master mechanism when the person manipulates a master manipulator based on the corrected force information transmitted from the force transmitting unit; and causing a slave control unit that is connected to the slave mechanism and the master control unit to output a control signal that transmits the manipulation information of the master mechanism sent from the master control unit to the slave mechanism.

With the configuration, even though the slave mechanism and the master mechanism have different inertia forces, the master mechanism can be prevented from being largely moved due to application of large force to the master mechanism, and, even though correction is performed to prevent the master mechanism from being largely moved, the person can feel a fed-back force.

13th aspect: A computer-readable recording medium including a program a control program for a master-slave robot that controls a master-slave device comprising a slave mechanism that grips an object and performs a task while being in contact with an object to be treated and a master mechanism that causes a person to remotely-manipulate the slave mechanism, the control program causing a computer to execute the steps of:

causing a force information acquiring unit to acquire force information of an external force acting on the slave mechanism;

causing a force correction determination unit, based on at least one piece of information of the force information and velocity information of the slave mechanism, to determine a force correction part serving as information of a section from a correction start time serving as start time of correction of the force information to a correction end time serving as end time of the correction and, as a correcting method, any one of two methods including a first method that determines a gain such that a reduction in an absolute value of the force information of the force correction part at the force correction part is maintained for a predetermined period of time to perform correction and a second method that determines a gain such that a reduction and an increase in the absolute value of the force information of the force correction part at the force correction part are repeated within a range that is not more than a value obtained by reducing the absolute value, to perform correction;

causing a force correction unit to correct the force information acquired by the force information acquiring unit by the correcting method determined by the force correction determination unit based on the correction part and the gain that are determined by the force correction determination unit;

causing a force transmitting unit to transmit, to the master mechanism, force information after the correction is performed by the force correction unit;

causing a master control unit to control manipulation information of the master mechanism when the person manipulates a master manipulator based on the corrected force information transmitted from the force transmitting unit; and causing a slave control unit that is connected to the slave mechanism and the master control unit to output a control signal that transmits manipulation information of the master mechanism sent from the master control unit to the slave mechanism.

With the configuration, even though the slave mechanism and the master mechanism have different inertia forces, the master mechanism can be prevented from being largely moved due to application of large force to the master mechanism, and, even though correction is performed to prevent the master mechanism from being largely moved, the person can feel a fed-back force.

First Embodiment

An outline of the master-slave device (master-slave robot) 100 according to a first embodiment of the present invention will be described below. A portion obtained by removing a slave mechanism 40 and a master mechanism 33 from the master-slave device 100 is also called a control apparatus for a master-slave robot.

FIG. 1 shows a manner of endoscopic surgery that is performed such that a manipulation by an operator 6a causes a slave robot 26 to insert an instrument in the body of a living body 4 through the use of the master-slave device 100. The master-slave device 100 includes the slave mechanism 40 having the slave robot 26 that grips an instrument serving as an example of an object, for example, forceps 2, 2a, 2b and performs a task while touching the human body 4 serving as a patient serving as an example of an object to be treated, and the master mechanism 33 having a master robot 25 through which a person (operator) 6 remotely-manipulates the slave mechanism 40.

When the operator 6 manipulates the master robot 25 while checking a video image (image) image-picked up by an endoscope 7 through a monitor 17a, the slave robot 26 that grips the forceps 2a, 2b operates. The following description, depending on situations, with respect to the forceps 2a and the forceps 2b, will be made by using the forceps 2a as a typical example.

Trocars 18a, 18b, and 18c are inserted into a plurality of (for example, three) holes formed in the abdomen of the human body 4, respectively, and then the forceps 2a, the forceps 2b, and the endoscope 7 are inserted into the holes of the trocars 18a, 18b, and 18c, respectively.

In the force measurement device 1, i.e., a force measurement device 1a and a force measurement device 1b, for example, the forceps 2a and the forceps 2b are directly gripped as integrated bodies or the forceps 2a and the forceps 2b are fixed to a tip end of the slave robot 26 gripped with a hand or the like. The force measurement device 1a and the force measurement device 1b are disposed at positions where the force measurement device 1a and the force measurement device 1b do not enter the body before and after the forceps 2a and the forceps 2b are inserted into the body. As another example, the force measurement device 1a and the force measurement device 1b may be fixed between the tip end of the slave robot 26 and an abdominal wall 3 of the living body 4. In other words, the force measurement device 1a and the force measurement device 1b are always disposed outside the body. The force measurement device 1 (1a, 1b) measures, outside the body, forces acting when the forceps 2a and the forceps 2b are inserted into the trocar 18a and the trocar 18b, respectively, a force acting on the abdominal wall 3, or a force generated when the tip end of the forceps 2a, 2b acts on an internal organ 5. The force measured by the force measurement device 1a, 1b is fed back from the slave robot 26 to the master robot 25, so that the operator 6 can manipulate the slave robot 26 with a manipulation feeling as if the operator directly manipulates the forceps 2a, 2b. Furthermore, the force detected by the force measurement device 1a, 1b is displayed together with a video image on the monitor 17a. When each of the force measurement devices 1a, 1b decides that a load is applied to the abdominal wall 3 or the internal organ 5, the operator 6 is notified through a loudspeaker 17b.

In this example, as the force measurement device 1, a force measurement device 1a is used for the forceps 2a, and a force measurement device 1b is used for the forceps 2b. Each of the force measurement device 1a and the force measurement device 1b has the same configuration as that of force measurement device 1.

The start and end instructions of force measurement of each of the force measurement devices 1a, 1b is performed by an input IF 8 disposed on a side surface of a surgical bed 70 such that the master robot 25 is manipulated to perform an inserting task of the slave robot 26 in conjunction with the start and end. The input IF 8 is a manipulation interface that is disposed in, for example, a lower portion of the surgical bed 70 and causes the operator 6 to instruct the start and end of measurements of the force measurement devices 1a,1b, and the input IF 8 is configured by, for example, a button or the like.

Figure 2:
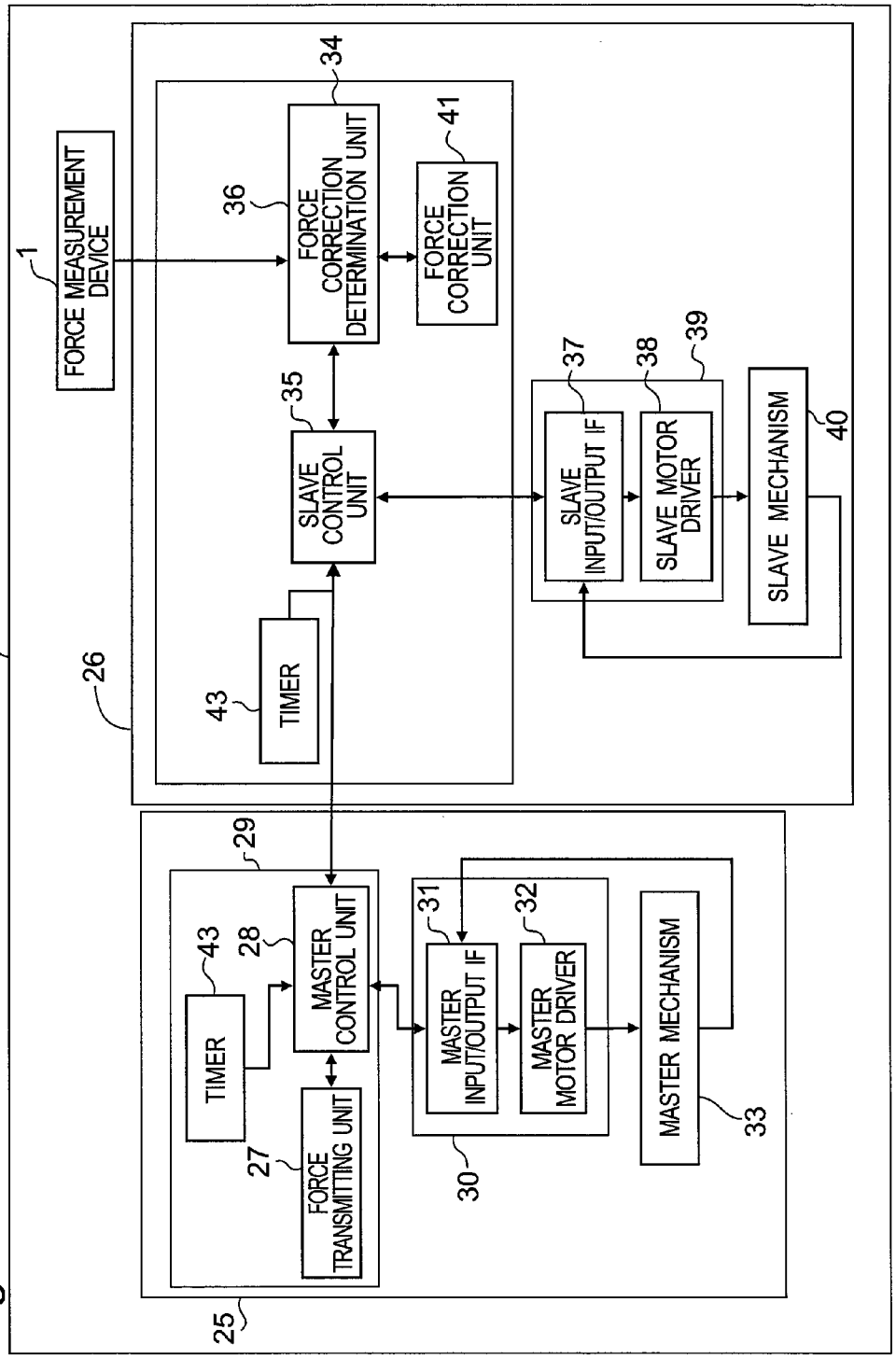
FIG. 2 is a block diagram showing a detailed configuration of the master-slave device according to the first embodiment of the present invention.
Figure 3:
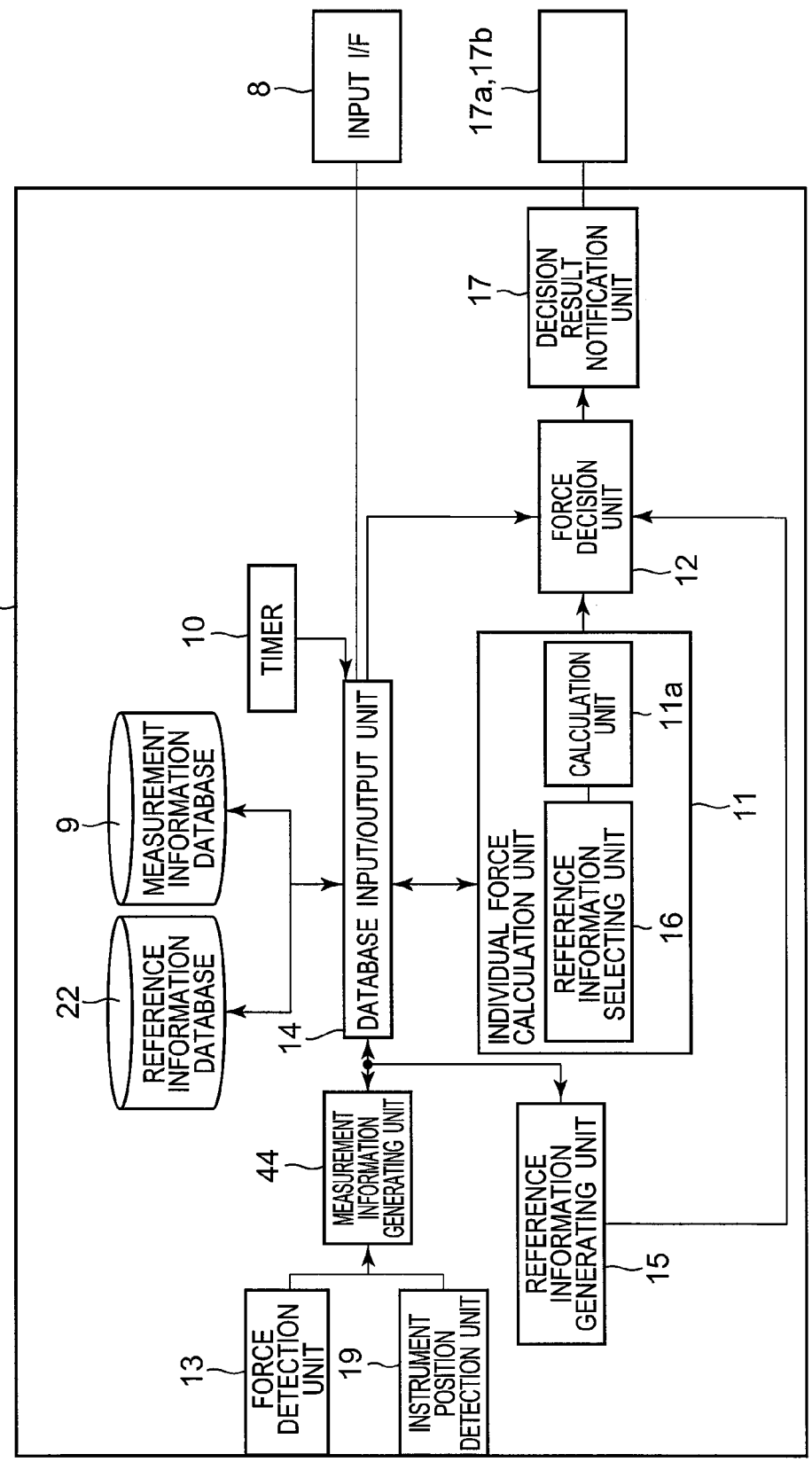
FIG. 3 is a block diagram showing a detailed configuration of a force measurement device according to the first embodiment of the present invention.

Next, details of the master robot 25, the slave robot 26, and the force measurement devices 1a, 1b according to the first embodiment will be described below. FIG. 2 is a block diagram of the master robot 25, the slave robot 26, and the force measurement devices 1a, 1b. FIG. 3 shows a detailed block diagram of the force measurement devices 1a, 1b.

<<Force Measurement Device 1>>

The force measurement device 1 (1a, 1b) is disposed outside a body and individually measures a force acting on the abdominal wall 3 and a force acting on the tip end of the forceps 2a, 2b. The force measurement device 1 (1a, 1b) serves as one example of a force information acquiring unit. From the force measurement devices 1a, 1b, an output value from a force detection unit 13, an individual force detected by an individual force detection unit 11, and a decision result obtained in a force decision unit 12 are output to a force correction determination unit 36 (will be described later) of the slave robot 26.

Each of the force measurement devices 1a, 1b according to the first embodiment includes the force detection unit 13, a database input/output unit 14, a measurement information database 9, a reference information database 22, a timer 10, an instrument position detection unit 19, a reference information generating unit 15, the individual force calculation unit 11, the force decision unit 12, and a decision result notification unit 17.

<<Force Detection Unit 13>>

The force detection unit 13 is another example of the force information acquiring unit and detects, from outside the human body 4, information of a force generated when the forceps 2a or the forceps 2b is brought into contact with the trocar 18a or 18b or the human body 4. For example, as an example of the force detection unit 13, a one-axis force sensor that measures a force in a one-axis direction, i.e., an insertion direction is employed, and, as shown in FIG. 1, the one-axis force sensor is disposed on each of out-of-body portions of the forceps 2a and 2b and at the tip end of the slave robot 26. A force T1 acting as a load applied to the abdominal wall 3 when the operator 6 manipulates the master robot 25 to manipulate the forceps 2a or the forceps 2b and to cause the forceps 2a or 2b passes through the trocar 18a or 18b, and a force T2 generated when the tip end of the forceps 2a or 2b acts on the internal organ 5 are summed up and measured.

Figure 4:
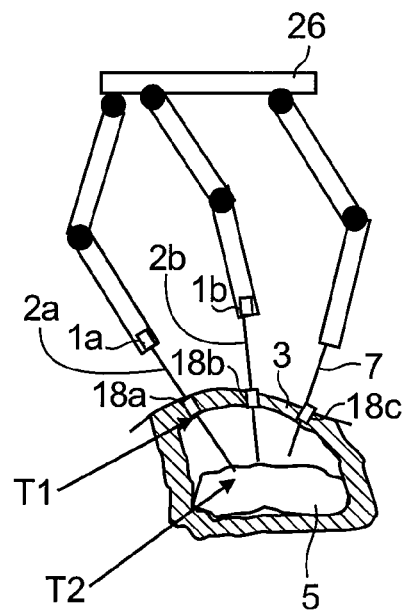
FIG. 4 is a view for describing a manipulation of endoscopic surgery in the first embodiment of the present invention.

For example, when the forces T1 and T2 are generated at the portions of the human body 4 as shown in FIG. 4, since the force detection unit 13 cannot individually detect the forces T1 and T2, the force detection unit 13 measures a sum T (in this example, T=T1+T2) of the respective forces. The values of the forces detected by the force detection unit 13 are detected by the force detection unit 13 every predetermined period of time (for example, every 4 msec) through the use of the timer 10 (will be described later), are output together with time from the force detection unit 13 to the database input/output unit 14 (will be described later), and are stored in the measurement information database 9 or the reference information database 22.

As the force detection unit 13 according to the first embodiment, as an example, a one-axis force sensor that detects only a force in a one-axis direction is used. However, alternatively, as another example of the force detection unit 13, a force sensor that can measure forces in 3-axis directions, i.e., x, y, and z axes, or a 6-axis force sensor that can measure the forces in the 3-axis directions and torques around the 3-axis directions may be used.

<<Timer 10>>

The timer 10 is connected to the database input/output unit 14 and outputs a command to execute the database input/output unit 14 after a predetermined period of time (for example, every 4 msec) has elapsed.

<<Database Input/Output Unit 14>>

The database input/output unit 14 performs data exchange among the measurement information database 9, the reference information database 22, the force detection unit 13, the instrument position detection unit 19, the reference information generating unit 15, the individual force calculation unit 11, and the force decision unit 12.

<<Instrument Position Detection Unit 19>>

Figure 5:
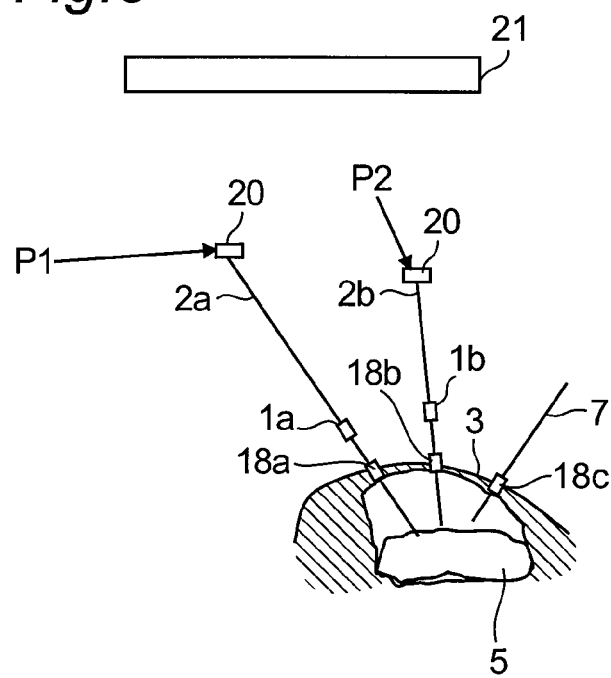
FIG. 5 is a view for describing an example of an instrument position detection unit according to the first embodiment of the present invention.

The instrument position detection unit 19 serves as one example of a position orientation acquiring unit that acquires positions or orientations of the forceps 2a and the forceps 2b inserted into the body. More specifically, the instrument position detection unit 19 detects respective tip-end positions (positions P1 and P2 in FIG. 5) of the forceps 2a and the forceps 2b on an opposite side of the internal organ 5 to output the positions to the database input/output unit 14 and the reference information generating unit 15. For example, the instrument position detection unit 19 is configured by a 3-axis magnetic position measurement sensor shown in FIG. 5, magnetic force measurement units 20 are attached to the tip-end positions (positions P1 and P2 in FIG. 5) of the forceps 2a and 2b on the opposite side of the internal organ 5, and a magnetic field is generated by a magnetic field source 21 to cause the instrument position detection unit 19 to detect the positions P1 and P2 of the forceps 2a and 2b. Information of the positions detected by the instrument position detection unit 19 is detected every predetermined period of time (for example, every 4 msec) through the use of the timer 10, is output together with time from the instrument position detection unit 19 to the database input/output unit 14 (will be described later), and is stored in the measurement information database 9 or the reference information database 22.

As an example, the instrument position detection unit 19 according to the first embodiment is of a magnetic type. However, as another example of the instrument position detection unit 19, a hand position of the slave robot 26 that grips the forceps 2a and the forceps 2b may be used. As still another example of the instrument position detection unit 19, a scheme in which markers are disposed at the tip-end positions (positions P1 and P2 in FIG. 5) of the forceps 2a and the forceps 2b on the opposite side of the internal organ 5 and the marker positions of the tip ends of the forceps are detected by using a camera, or a scheme in which the tip ends of the forceps are detected by an infrared sensor may be used. Although the tip-end positions of the forceps $2a$ and $2b$ are detected in coordinates of 3-axis directions, when the forceps $2a$ and the forceps $2b$ move in a direction orthogonal to the insertion direction with reference to the trocar $18a$ at a part of the abdominal wall 3, in order to specify the positions of the forceps $2a$ and $2b$, coordinates (coordinates of 3-axis directions and coordinates of rotational angles around the axes) of 6-axis directions in which the positions and the orientations of the forceps $2a$ and $2b$ can be measured may be detected.

<<Reference Information Generating Unit 15>>

The reference information generating unit 15, based on pieces of information from the instrument position detection unit 19, the force detection unit 13, and the database input/output unit 14, generates reference information relating to a force and outputs the reference information to the database input/output unit 14 and the force decision unit 12 while the forceps $2a$, $2b$ are not in contact with a surgery site 5. The reference information is information relating to a force acquired when the manipulation by the operator 6 causes the slave robot 26 to move the forceps $2a$, $2b$ in a predetermined direction in a state in which the tip ends of the forceps $2a$, $2b$ pass through the abdominal wall 3, are inserted into the body of the living body 4, and are not in contact with the surgery site 5. The reference information is used when forces generated when the forceps $2a$, $2b$ act inside the body are individually calculated from outside the body (individual force is calculated). More specifically, the reference information is information configured by pairing: the positions (moving direction of the forceps $2a$) or the orientations of the forceps $2a$, $2b$ detected by the instrument position detection unit 19 before the forceps $2a$, $2b$ pass through the abdominal wall 3, are inserted into the body, and are brought into contact with the internal organ 5; a value of a force detected by the force detection unit 13; a reference information basing point calculated by a method (will be described later); and time. The force information included in the reference information is also called displacement information of time-series forces.

The reference information basing point is set to a time point at which a displacement of a force detected by the force detection unit 13 changes by a predetermined first threshold value (threshold value for setting basing point or threshold value for setting first time point) (for example, 0.1 N) or more. The "reference information basing point" mentioned here means a time point serving as a reference for individually measuring (calculating) forces that respectively act based on the sum of forces detected by the force detection unit 13. The reference information generating unit 15 sets a start point of reference information generation as a first basing point.

Movement of the forceps $2a$, $2b$ is started by driving the slave robot 26 in response to a reference information generation start command generated from the input IF 8 through the database input/output unit 14, and the reference information generating unit 15 generates the pieces of reference information every predetermined period of time (for example, every 4 msec) through the use of the timer 10. The reference information generated by the reference information generating unit 15 is output to the database input/output unit 14 together with time and stored in the reference information database 22.

More specifically, as shown in FIGS. 10B to 10E of FIGS. 10A to 10E, information of a position and a force of the forceps $2a$ in a state in which the forceps $2a$ is caused to pass through the abdominal wall 3 through the trocar $18a$ from outside the body and has a tip end on the inner side of the body that is not in contact with the internal organ 5 is acquired by the reference information generating unit 15, a basing point is calculated by the reference information generating unit 15 based on the information of the force, and reference information obtained by pairing the position and the force of the forceps $2a$ and the reference point is generated by the reference information generating unit 15. At a time point in FIG. 10A, since the forceps $2a$ has not passed through the abdominal wall 3 through the trocar $18a$ yet, the reference information has not been generated by the reference information generating unit 15. For this reason, when the forceps $2a$ reaches a position shown in FIG. 10B, the operator 6 instructs the force measurement device $1a$ to start generation of reference information through the use of the input IF 8.

In this case, as shown in FIGS. 10A to 10E, a description will be given of an example of a task in which the forceps $2a$ is inserted from a hole formed in the abdominal wall 3 into a human body 4 through the trocar $18a$ in a downward direction from above the human body 4. States in FIG. 10B to FIG. 10E are states in each of which the forceps $2a$ is not in contact with the internal organ 5 and reference information is generated. Thus, the following reference information generating operation is performed in states in FIGS. 10A to 10E.

First, when receiving a start command for force measurement via the input IF 8, the force measurement device $1a$ starts force measurement.

Figure 10A:
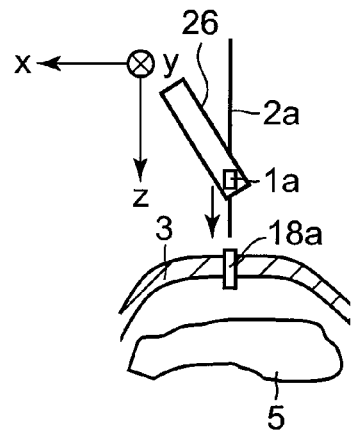
FIG. 10A is a view for describing a manipulation of the endoscopic surgery in the first embodiment of the present invention.
Figure 10B:
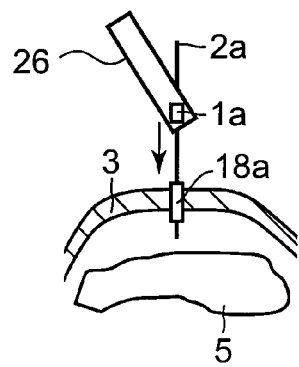
FIG. 10B is a view for describing a manipulation of the endoscopic surgery in the first embodiment of the present invention.
Figure 10C:
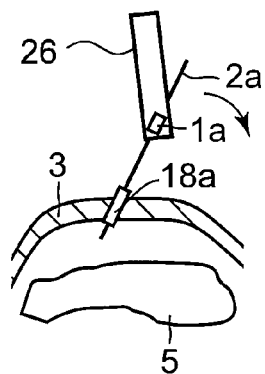
FIG. 10C is a view for describing a manipulation of the endoscopic surgery in the first embodiment of the present invention.
Figure 10D:
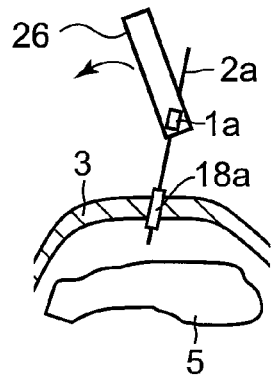
FIG. 10D is a view for describing a manipulation of the endoscopic surgery in the first embodiment of the present invention.
Figure 10E:
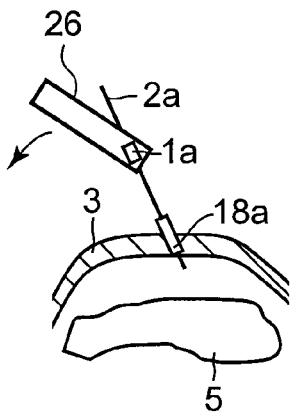
FIG. 10E is a view for describing a manipulation of the endoscopic surgery in the first embodiment of the present invention.
Figure 10F:
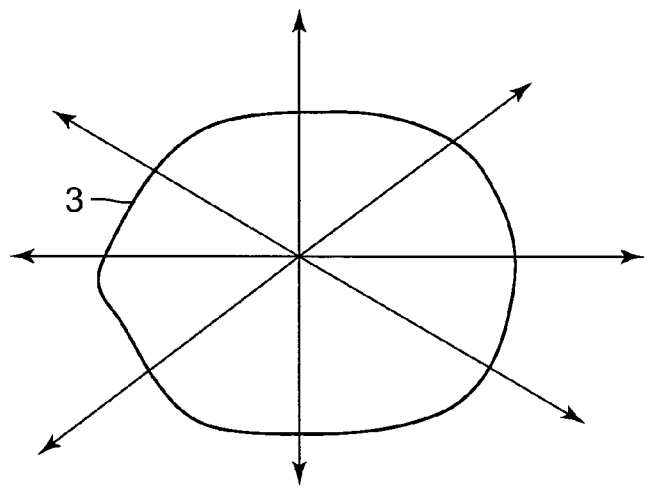
FIG. 10F is a view for describing a manipulation of the endoscopic surgery in the first embodiment of the present invention.
Figure 10G:
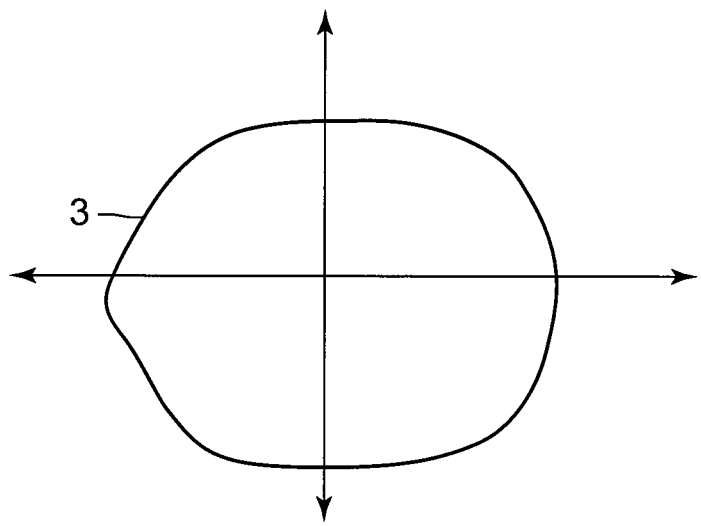
FIG. 10G is a view for describing a manipulation of the endoscopic surgery in the first embodiment of the present invention.
Figure 10H:
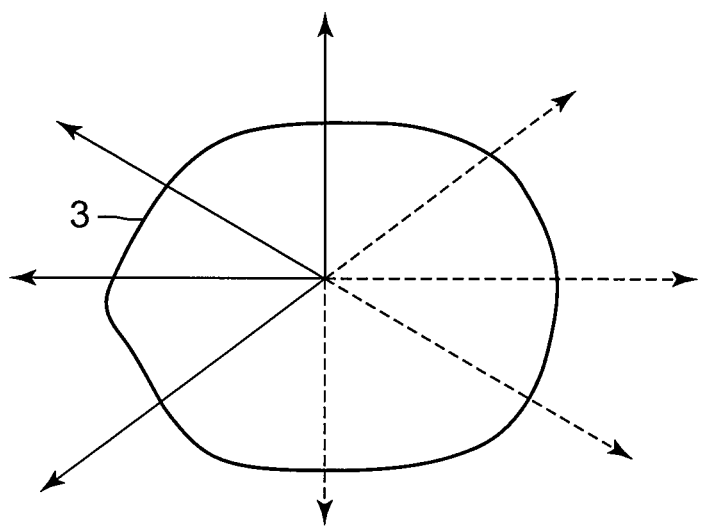
FIG. 10H is a view for describing a manipulation of the endoscopic surgery in the first embodiment of the present invention.
Figure 10I:
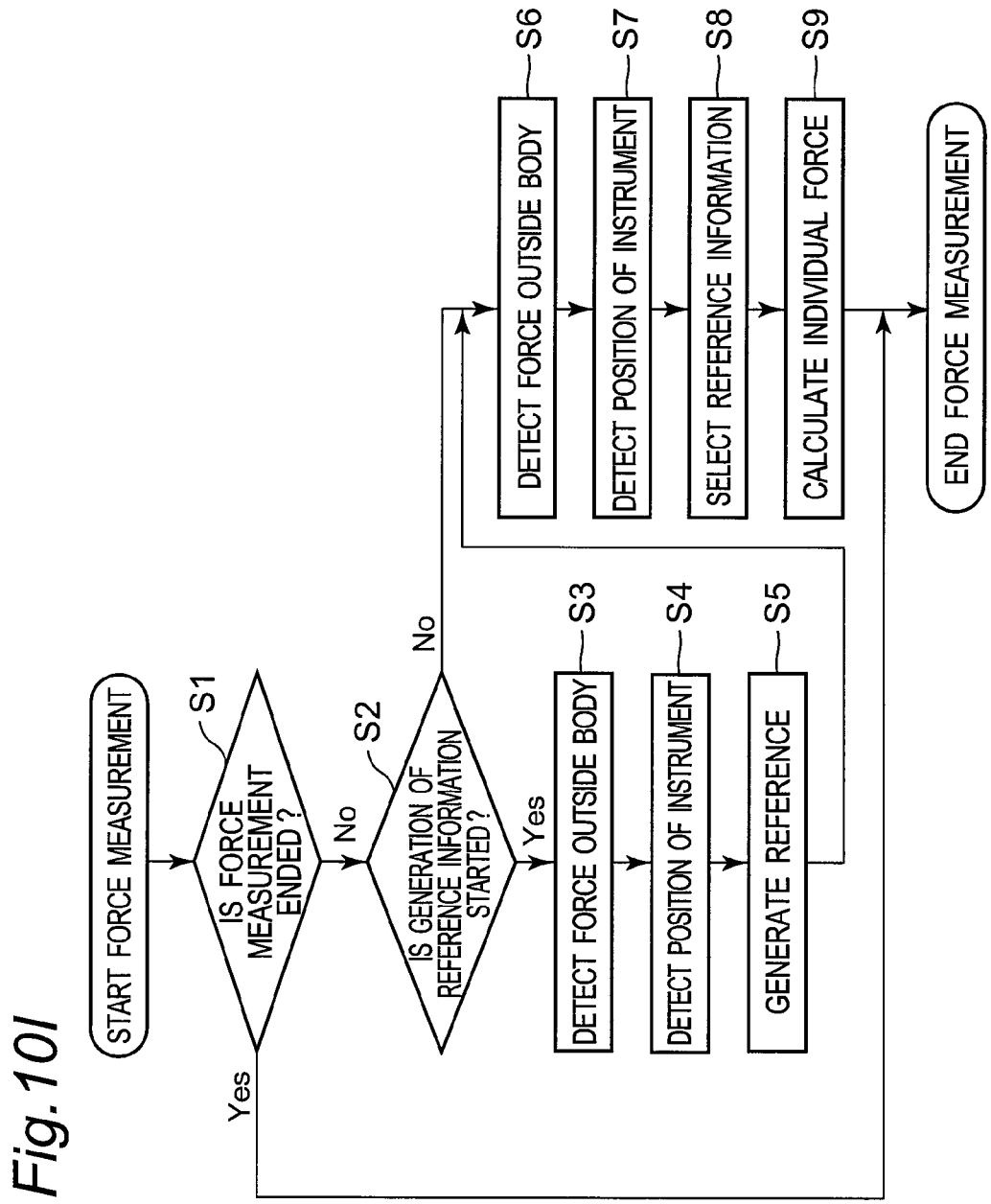
FIG. 10I is a flow chart of a force measurement process of the force measurement device according to the first embodiment of the present invention.

Next, in step S1 in FIG. 10I, when receiving an end command for force measurement via the input IF 8, the force measurement device $1a$ ends the force measurement. When the end command for force measurement is not input, the force measurement process proceeds to next step S2.

Next, in step S2, when a generation start command for reference information is input via the input IF 8, the force measurement process proceeds to step S3. When a generation start command for reference information is not input, the force measurement process proceeds to step S6. For example, when the process proceeds to steps S3 and S4 and reference information is generated in step S5 once in one surgical operation, in the next and subsequent surgical operations, there is no reference information generation start command in step S2, and the reference information that has been already generated can be used without generating reference information.

Figure 9A:
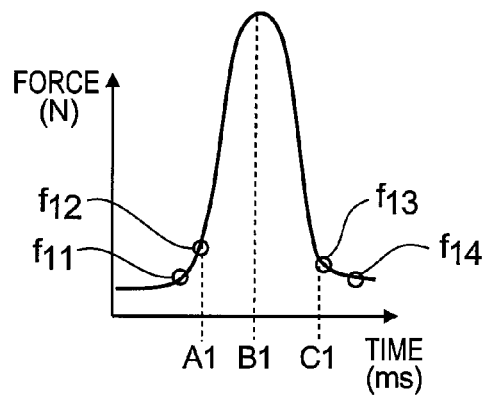
FIG. 9A is a graph showing a time-series change of a force in the first embodiment of the present invention.
Figure 9B:
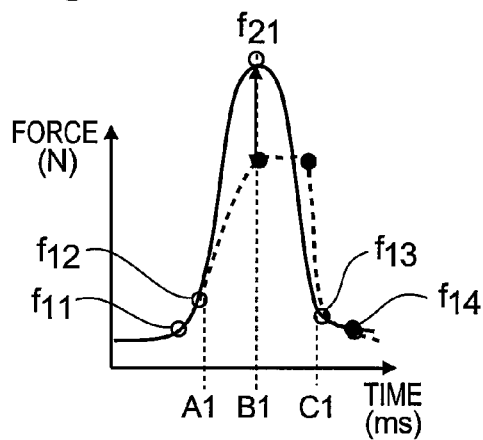
FIG. 9B is a graph showing a time-series change of a force in the first embodiment of the present invention.
Figure 9C:
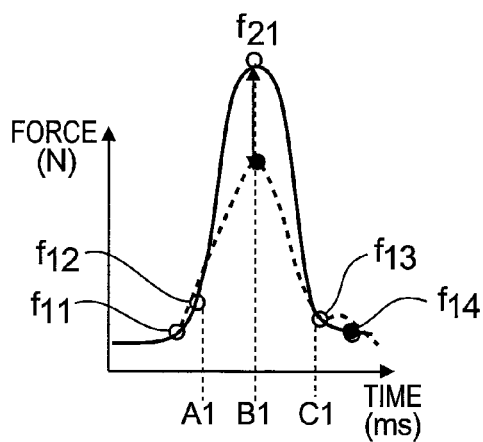
FIG. 9C is a graph showing a time-series change of a force in the first embodiment of the present invention.

Next, in step S3, in a state in which the forceps $2a$ is inserted into the body and is not in contact with the internal organ 5 in FIGS. 10A to 10B or 10C, the force detection unit 13 detects a force acting on the forceps $2a$ serving as an example of an instrument, from outside the body (see FIGS. 9B and 9C).

Next, in step S4, in a state in which the forceps $2a$ is not in contact with the internal organ 5, the instrument position detection unit 19 detects a position of the forceps $2a$ from outside the body (see FIGS. 10B and 10C).

Next, in step S5, the reference information generating unit 15 generates reference information by calculating a basing point based on the force detected in step S3 and the position of the forceps $2a$ detected in step S4. More specifically, as shown in FIGS. 10B to 10E of FIGS. 10A to 10E, information of a position and a force of the forceps $2a$ in a state in which the forceps $2a$ is caused to pass through the abdominal wall 3 from outside the body and has a tip end on the inner side of the body that is not in contact with the internal organ 5 is acquired by the reference information generating unit 15. More specifically, the forceps $2a$ is inclined from a central position (see FIG. 10B) in one direction to acquire reference information (see FIGS. 10B and 10C). Thereafter, after the forceps $2a$ is returned to the central position (see FIG. 10D) again, the forceps $2a$ is moved to be inclined in the next other direction to acquire another piece of reference information (see FIGS. 10D to 10E). Hereinafter, in this manner, pieces of reference information are acquired with respect to predetermined directions. Next, a basing point is calculated based on the information of the force in the reference information generating unit 15. Next, reference information obtained by pairing the position and the force of the forceps 2a with the basing point is generated by the reference information generating unit 15. FIG. 10F is a view showing the structures in FIGS. 10A to 10E when viewing from above. As shown in FIG. 10F, in a state in which the tip end of the forceps 2a passes through the abdominal wall 3, is inserted into the body of the living body 4, and is not in contact with the surgery site 5, the operator 6 manipulates the slave robot 26 to move the forceps 2a in predetermined directions from the center so as to cause the reference information generating unit 15 to generate reference information. In this case, the predetermined direction is, for example, eight directions (upper and lower, left and right, obliquely upper right, obliquely upper left, obliquely lower right, and obliquely lower left directions) including four directions orthogonal to each other. The forceps 2a is moved such that the forceps 2a is inclined in one direction from the central position, returned to the central position again, and then inclined in the next other direction. When the reference information is generated, a direction in which the forceps 2a is moved from the central position is not limited to the eight directions. At least the forceps 2a must be moved in at least two directions (for example, a muscle fiber direction and a direction orthogonal to the muscle fiber direction or a longitudinal direction of the trocar 8a, a direction in which the forceps 2a comes close to a surgery site with reference to the central position of the forceps 2a located to have a longitudinal direction parallel to the longitudinal direction of the trocar 8a, and a direction orthogonal to the direction in which the forceps 2a comes close to the surgery site) intersecting with a direction in which the forceps 2a is inserted into the body. At this time, the forceps 2a is kept from coming in contact with an internal organ at all. At a time point in FIG. 10A, since the forceps 2a has not passed through the abdominal wall 3 yet, the reference information has not been generated by the reference information generating unit 15. For this reason, when the forceps 2a reaches a position shown in FIG. 10B, the operator 6 manipulates the input IF 8 to start generation of reference information.

In the first embodiment, the forceps 2a is operated as shown in FIG. 10F. However, the operation of the forceps 2a is not limited to that shown in FIG. 10F. For example, operating directions of the forceps 2a are defined as four directions as shown in FIG. 10G, or the forceps 2a may be operated in only directions of solid lines shown in FIG. 10H, and, with respect to each of diagonal directions (directions of dotted lines shown in FIG. 10H), a sign may be inverted to automatically generate reference information in the reference information generating unit 15.

In step S2 to step S5 described above, the reference information generating operation is performed.

The following operation is a force measurement process performed by using the generated reference information, and will be briefly described below.

Figure 12A:
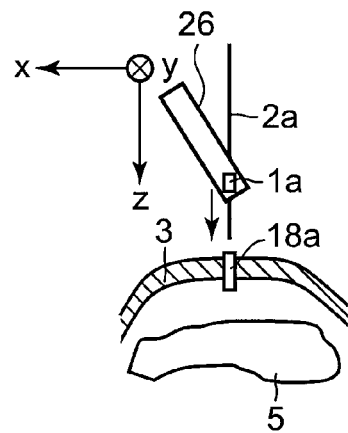
FIG. 12A is a view for describing a manipulation of the endoscopic surgery in the first embodiment of the present invention.
Figure 12B:
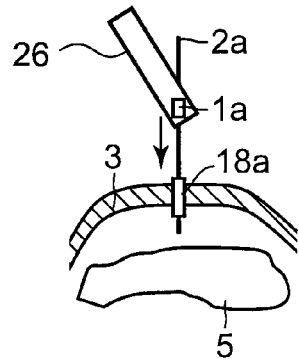
FIG. 12B is a view for describing a manipulation of the endoscopic surgery in the first embodiment of the present invention.
Figure 12C:
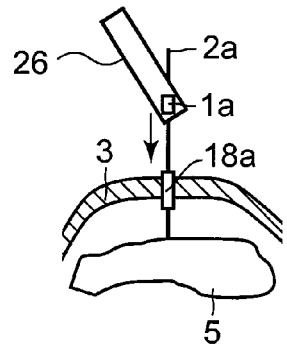
FIG. 12C is a view for describing a manipulation of the endoscopic surgery in the first embodiment of the present invention.

Next, in step S6, as shown in FIG. 12C, at a time point at which the tip end of the forceps 2a is in contact with the internal organ 5, the force detection unit 13 detects a force acting from outside the body to the forceps 2a.

Next, in step S7, the instrument position detection unit 19 detects a position of the forceps 2a from outside the body.

Next, in step S8, the reference information selecting unit 16 selects reference information for calculating an individual force.

Next, in step S9, based on the reference information selected by the reference information selecting unit 16, a calculation unit 11a of the individual force calculation unit 11 calculates an individual force.

This is the end of the force measurement process.

Figure 11:
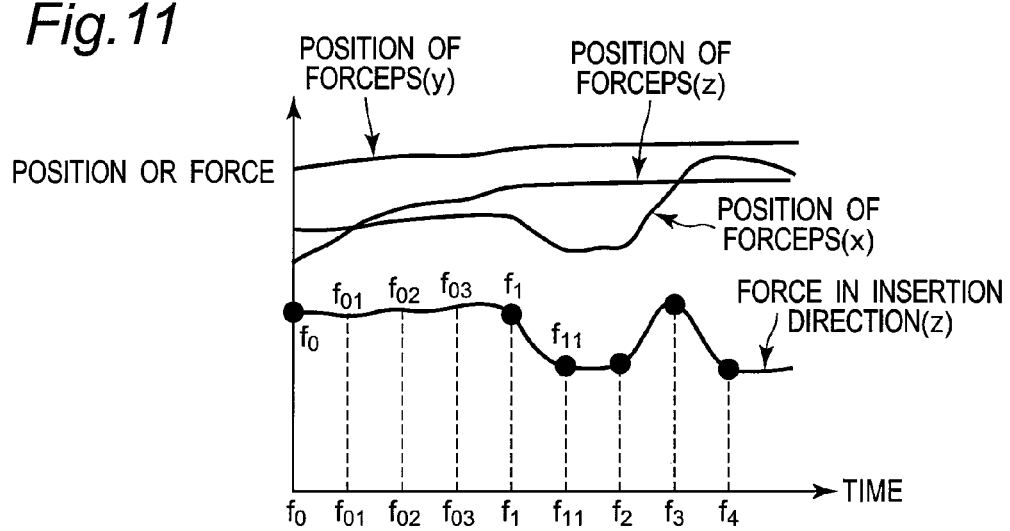
FIG. 11 is a graph showing a relationship between a force in an insertion state and a position of an instrument in the first embodiment of the present invention.

FIG. 11 is a graph showing, as in FIGS. 10B to 10E, relationship between time and the positions and the forces of the forceps 2a from a time point when generation of the reference information is started by the input IF 8. The insertion direction of the forceps 2a is defined as a z axis, and directions orthogonal to the insertion direction are defined as an x axis and a y axis, respectively.

A time point when generation of the reference information is started (the time point $t_0$ in FIG. 11) is set as the first basing point by the reference information generating unit 15. Next, in a state in which the operator 6 manipulates the slave robot 26 to cause the tip end of the forceps 2a to pass through the abdominal wall 3, to be inserted into the body of the living body 4, and not to be in contact with the surgery site 5, the reference information generating unit 15 compares absolute values of displacements of forces detected by the force detection unit 13 each time a predetermined period of time has passed while moving the forceps 2a in a predetermined direction, and a time point at which the difference changes by a predetermined first threshold value (for example, 0.1 N) or more is set as a basing point by the reference information generating unit 15. More specifically, a force obtained at a basing point $t_0$ in FIG. 11 is represented by $f_0$, a force obtained at a time point $t_{01}$ is represented by $f_{01}$, and a force obtained at a time point $t_{02}$ is defined as $f_{02}$. In this case, $\Delta f_{01}=|f_{01}-f_0|$ and $\Delta f_{02}=|f_{02}-f_{01}|$ are compared with each other by the reference information generating unit 15. Next, the reference information generating unit 15 calculates the difference to check whether the difference is the predetermined first threshold value or more. In this example, since the difference is less than the predetermined first threshold value, the reference information generating unit 15 does not set the time point $t_{01}$ as a basing point. Next, the reference information generating unit 15 sequentially compares displacements of forces obtained every predetermined period of time with each other. Next, a force obtained at a time point $t_{03}$ is represented by $f_{03}$, a force obtained at a time point $t_1$ is represented by $f_1$, and a force obtained at a time point $t_{11}$ is represented by $f_{11}$. Next, the reference information generating unit 15 compares $\Delta f_1=|f_1-f_{03}|$ and $\Delta f_{11}=|f_{11}-f_1|$ with each other. Next, the reference information generating unit 15 determines whether the difference is the predetermined first threshold value or more. In this example, since the difference is the predetermined first threshold value or more, the reference information generating unit 15 sets the time point $t_1$ as a basing point. Next, in a similar manner, the reference information generating unit 15 sequentially sets basing points. The set basing point is represented by a black circle "●" in FIG. 11. Next, the set basing point is generated by the reference information generating unit 15 as reference information obtained by pairing a force and a position every predetermined period of time (for example, every 4 msec) through the use of the timer 10, is output from the reference information generating unit 15 to the database input/output unit 14 together with time, and is stored in the reference information database 22, and via the input IF 8, a command for ending the generation of reference information is input. More specifically, in a state in which the tip end of the forceps 2a passes through the abdominal wall 3, is inserted into the body of the living body 4, and is not in contact with the surgery site 5, at a time point at which the operator 6 manipulates the slave robot 26 to cause the forceps 2a to have moved in the predetermined direction, the operator 6 inputs via the input IF 8 a command for ending the generation of reference information.

—Reference Information Database 22—

The reference information database 22 stores the reference information generated by the reference information generating unit 15 through the database input/output unit 14 together with time through the use of the timer 10. As needed, the reference information is read from the reference information database 22 by the database input/output unit 14. The reference information, as described above, is information configured by pairing information relating to a force detected by the force detection unit 13, positions of the forceps 2a, 2b obtained by the instrument position detection unit 19 before the forceps 2a, 2b are brought into contact with the internal organ 5, a basing point calculated by the reference information generating unit 15, and time.

More specifically, out of the reference information, the information relating to the force detected by the force detection unit 13, the positions of the forceps 2a, 2b detected by the instrument position detection unit 19 before the forceps 2a, 2b are brought into contact with the internal organ 5, and the basing point calculated by the reference information generating unit 15 are generated by the reference information generating unit 15 every predetermined period of time (for example, every 4 msec) through the use of the timer 10, are output from the reference information generating unit 15 to the database input/output unit 14 together with time, and are stored in the reference information database 22.

FIG. 6 shows an example of the contents of the reference information of the reference information database 22.

(1) A column for "time" shows information relating to time at which the forceps 2a and 2b are inserted. In the first embodiment, the time is shown in units of milliseconds (msec).

(2) A column for "force" shows information of a force detected by the force detection unit 13. In the first embodiment, the force in an insertion direction is shown in units of newton (N), and the force in a rotational direction is shown in units of newton meter (Nm).

(3) A column for "position" shows respective positions of the forceps 2a and 2b detected by the instrument position detection unit 19. In the first embodiment, the position is shown in units of meter (m).

(4) A column for "basing point" shows a basing point set by the reference information generating unit 15. "1" is set in the corresponding time column when the basing point is set, "0" is set in the corresponding time column when the basing point is not set, and "0" is set as a default value.

(5) A column for "ID" shows a sign used to identify reference information. More specifically, the same ID is set in a period of time from a basing point set by the reference information generating unit 15 to the next basing point.

<<Measurement Information Generating Unit 44>>

The measurement information generating unit 44 generates measurement information based on the pieces of information from the instrument position detection unit 19, the force detection unit 13, and the database input/output unit 14 and outputs the measurement information to the database input/output unit 14. The measurement information includes information relating to the force detected by the force detection unit 13, positions of the forceps 2a and 2b detected by the instrument position detection unit 19 before and after the forceps 2a and 2b are brought into contact with the internal organ 5, and information of a force calculated by the calculation unit 11a of the individual force calculation unit 11 (will be described later).

—Measurement Information Database 9—

The information relating to the force detected by the force detection unit 13 and the positions of the forceps 2a, 2b detected by the instrument position detection unit 19 before and after the forceps 2a, 2b is brought into contact with the internal organ 5 are generated by the measurement information generating unit 15 through the database input/output unit 14 every predetermined period of time (for example, every 4 msec) through the use of the timer 10, are output from the measurement information generating unit 15 to the database input/output unit 14 together with time, and are stored in the measurement information database 9 as measurement information.

Furthermore, in the measurement information database 9, the pieces of information described above, the ID of the reference information selected by the reference information selecting unit 16 of the individual force calculation unit 11, the individual force calculated by the calculation unit 11a of the individual force calculation unit 11 are paired with time and stored. As needed, the measurement information from the measurement information database 9 is read from the database input/output unit 14.

FIG. 7 shows an example of the contents of the measurement information in the measurement information database 9.

(1) A column for "time" shows information relating to time at which the forceps 2a and 2b are inserted. In the first embodiment, the time is shown in units of milliseconds (msec).

(2) A column for "force" shows information of a force detected by the force detection unit 13. In the first embodiment, a force in an insertion direction is shown in units of newton (N), and a force in a rotational direction is shown in units of newton meter (Nm).

(3) A column for "position" shows positions and orientations of the forceps 2a and 2b detected by the instrument position detection unit 19. In the first embodiment, a position is shown in units of meter (m).

(4) A column for "ID of reference information" shows an ID of reference information selected by the reference information selecting unit 16 of the individual force calculation unit 11.

(5) A column for "individual force" shows information of a force calculated by the calculation unit 11a of the individual force calculation unit 11. In the first embodiment, a force in an insertion direction is shown in units of newton (N), and a force in a rotational direction is shown in units of newton meter (Nm).

<<Individual Force Calculation Unit 11>>

The individual force calculation unit 11, when the forceps 2a, 2b are brought into contact with the internal organ 5, individually calculates forces generated when the forceps 2a and 2b act on the internal organ 5 based on the information of the force detected by the force detection unit 13 and the reference information. More specifically, the individual force calculation unit 11, when the forceps 2a, 2b are inserted into the body of a living body, sets an individual force calculation basing point at which a displacement of the force detected by the force detection unit 13 is a third threshold value (threshold value for setting individual force calculation basing point) or more, sequentially searches positions close to the positions of the forceps 2a, 2b at the individual force calculation basing point based on the basing point of the reference information, causes the reference information selecting unit 16 to select reference information including the matched position obtained by the searching, and causes the calculation unit 11a to calculate, as an individual force, a value obtained by subtracting a force calculated based on the selected reference information from the force detected by the force detection unit 13. More specifically, in the calculation unit 11a of the individual force calculation unit 11, individual forces generated when the forceps 2a and 2b are brought into contact with the internal organ 5 are calculated based on the reference information stored in the reference information database 22 and the force detected by the force detection unit 13, through the database input/output unit 14. The reference information used in the reference information selecting unit 16 of the individual force calculation unit 11 is selected by the reference information selecting unit 16 based on the present (in a force measurement state) positions of the forceps 2a and 2b from the reference information read from the reference information database 22 by the database input/output unit 14.

The reference information selecting unit 16 selects reference information closest to the present (in a force measurement state) positions (however, positions of axes orthogonal to an insertion direction except for a position in the insertion direction) of the forceps 2a and 2b from positions of the forceps 2a and 2b before the forceps 2a and 2b pass through the abdominal wall 3 and the tip ends thereof are brought into contact with the internal organ 5. The ID of the reference information selected by the reference information selecting unit 16 is stored from the reference information selecting unit 16 in an "ID of reference information" of the measurement information database 9 through the database input/output unit 14.

The individual force calculation unit 11 detects individual forces acting when the forceps 2a and 2b are brought into contact with the internal organ 5, based on the reference information selected by the reference information selecting unit 16. More specifically, based on the reference information read from the reference information database 22 by the database input/output unit 14, the reference information selecting unit 16 selects reference information at a time point at which the reference information is desired to be measured (see step S8 in FIG. 10I). Next, a value obtained by subtracting a value of a force of the reference information selected by the reference information selecting unit 16 from the value of the force detection unit 13 at the time point is calculated by the calculation unit 11a of the individual force calculation unit 11 as an individual force (see step S9 in FIG. 10I). The individual force calculated by the calculation unit 11a of the individual force calculation unit 11 is stored from the calculation unit 11a of the individual force calculation unit 11 into the measurement information database 9 through the database input/output unit 14.

Figure 13A:
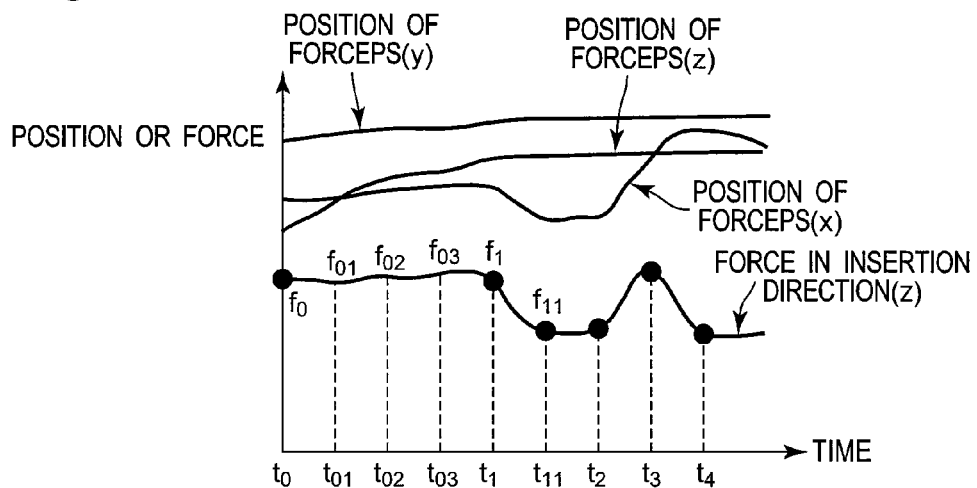
FIG. 13A is a graph showing a relationship between a force in an insertion state and a position of an instrument in the first embodiment of the present invention.
Figure 13B:
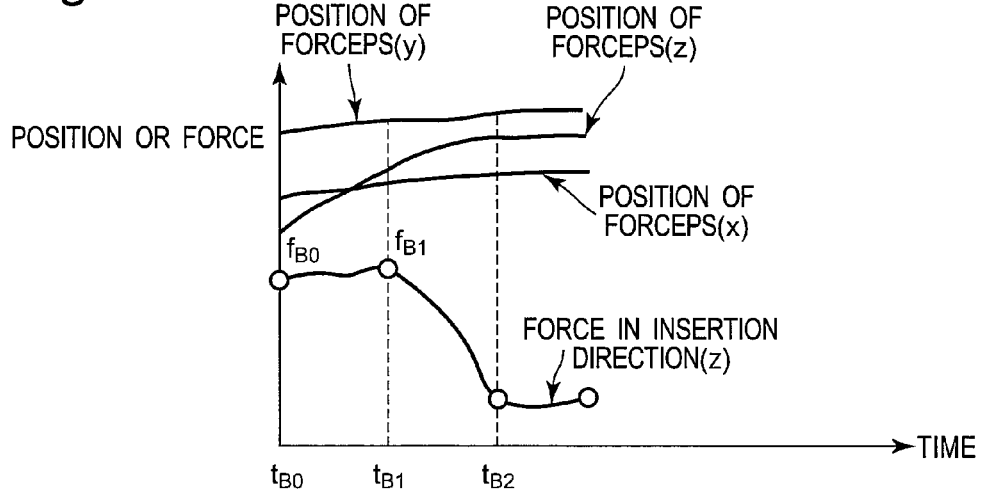
FIG. 13B is a graph showing a relationship between a force in an insertion state and a position of an instrument in the first embodiment of the present invention.

More specifically, FIG. 13A shows a graph of a position and a force of the forceps 2a and time in the reference information generated by the reference information generating unit 15. FIG. 13B is a graph of a position and a force of the forceps 2a and time obtained when the tip end of the forceps 2a is brought into contact with the internal organ 5 as shown in FIGS. 12B and 12C.

The reference information selecting unit 16 selects reference information closest to the position (however, a position of an axis orthogonal to an insertion direction except for a position in the insertion direction) of the forceps 2a in FIG. 12C.

More specifically, firstly, with respect to a force of the forceps 2a in FIG. 12C, a basing point for calculating an individual force is calculated by the calculation unit 11a of the individual force calculation unit 11. As a calculation method, as in the reference information generating unit 15, a time point at which a displacement of the force detected by the force detection unit 13 changes by a predetermined third threshold value (threshold value for setting individual force calculation basing point or threshold value for setting second time point) (for example, 0.1 N) or more is set as an individual force calculation basing point by the calculation unit 11a of the individual force calculation unit 11. The individual force calculation basing point mentioned here means a time point serving as a reference for individually calculating (measuring) forces that respectively act based on the sum of forces detected by the force detection unit 13. A start time point in FIG. 13B is set as the first basing point by the calculation unit 11a of the individual force calculation unit 11. A basing point set by the calculation unit 11a of the individual force calculation unit 11 is indicated by a white circle "○" in FIG. 13B. Next, every position of the forceps 2a between the basing points in FIG. 13B, except for a position in an insertion direction (z-axis direction in FIGS. 12C and 13B), a position of an axis (x-axis direction and y-axis direction in FIGS. 12C and 13B) orthogonal to the insertion direction, is compared with reference information in FIG. 13A at every basing point by the reference information selecting unit 16 of the individual force calculation unit 11. In this example, a position closest to time series information at the position of the forceps 2a in an x direction and a y direction in FIG. 13B is calculated from FIG. 13A by the calculation unit 11a of the individual force calculation unit 11. As an example of a method of calculating the closest position, with respect to a position x of the forceps 2a between a basing point A and a basing point B, a straight line is calculated by a least-square method in the calculation unit 11a of the individual force calculation unit 11, and an inclination and an intercept of the straight line are compared in the calculation unit 11a of the individual force calculation unit 11. By the above method, in the example, the reference information selecting unit 16 of the individual force calculation unit 11 decides that a section from a time point $t_0$ to a time point $t_1$ in FIG. 13A serving as reference information is closest to a section from the time point $t_{B0}$ to the time point $t_{B1}$ in FIG. 13B serving as measurement information.

Thus, reference information to calculate individual forces at the time point $t_{B0}$ to the time point $t_{B1}$ in FIG. 13B in the calculation unit 11a of the individual force calculation unit 11 is selected by the reference information selecting unit 16 as the time point $t_0$ to the time point $t_1$ in FIG. 13A. Similarly, pieces of reference information at the time point $t_{B1}$ to the time point $t_{B2}$ in FIG. 13B are selected by the reference information selecting unit 16. Thus, since the section from the time point $t_{B1}$ to the time point $t_{B2}$ in FIG. 13B is the same as the section from the time point $t_0$ to the time point $t_1$ in FIG. 13A, reference information to calculate individual forces at the time points $t_{B1}$ to $t_{B2}$ in FIG. 13B in the calculation unit 11a of the individual force calculation unit 11 are selected by the reference information selecting unit 16 as the time points $t_0$ to $t_1$ in FIG. 13A. The ID of the reference information selected by the reference information selecting unit 16 is stored from the reference information selecting unit 16 in an "ID of reference information" of the measurement information database 9 through the database input/output unit 14.

Next, based on the reference information selected by the reference information selecting unit 16, the calculation unit 11a of the individual force calculation unit 11 calculates an individual force (see step S9 in FIG. 10I). A value obtained by subtracting a force calculated based on the force of the reference information selected by the reference information selecting unit 16 from the force of the force detection unit 13 at the time point at which the individual forces are calculated by the calculation unit 11a of the individual force calculation unit 11 is calculated as an individual force by the calculation unit 11a of the individual force calculation unit 11. As an example of the method of calculating the subtracting force, a straight line is calculated by a least-square method in the calculation unit 11a of the individual force calculation unit 11 based on the force of the reference information of the selected section. A force f calculated by the calculation unit 11a of the individual force calculation unit 11 is given by f=at×b ("a" is an inclination, "b" is an intercept, "t" is time, and "f" is a force). By using the straight line, the subtracting force f is calculated by the calculation unit 11a of the individual force calculation unit 11, and the calculated force is subtracted from the force detected by the force detection unit 13, so that an individual force is calculated by the calculation unit 11a of the individual force calculation unit 11.

Figure 13C:
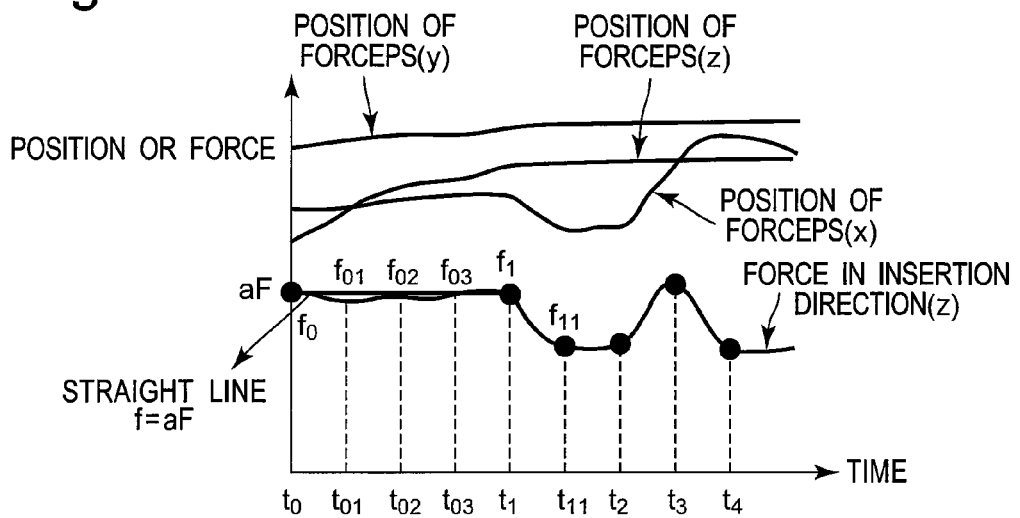
FIG. 13C is a graph showing a relationship between a force in an insertion state and a position of the instrument and time in the first embodiment of the present invention.

An example will be described in detail with reference to FIGS. 13A and 13B. Forces in a section of the selected reference information (the time point $t_0$ to the time point $t_1$ in FIG. 13A) are given as $f_0, f_{01}, f_{02} \ldots, f_1$ in FIG. 13A. A straight line is calculated by a least-square method using the forces $f_0, f_{01}, f_{02} \ldots, f_1$ in the calculation unit 11a of the individual force calculation unit 11. Since inclinations at the time points $t_0$ to $t_1$ in FIG. 13A become zero, a straight line given by f=aF is obtained as shown in FIG. 13C. The time points $t_0$ to $t_1$ in FIG. 13C show displacements of forces on time series. Next, individual forces at the time point $t_{B0}$ to the time point $t_{B1}$ in FIG. 13B are defined as values that are obtained by subtracting aF from the forces in the calculation unit 11a of the individual force calculation unit 11. More specifically, when the force at the time point $t_{B0}$ in FIG. 13B is given by $f_{B0}$, an individual force at the time point $t_{B0}$ is given by $f_{B0}$–aF. Similarly, when a force at the time point $t_{B1}$ is given by $f_{B1}$, an individual force at the time point $t_{B1}$ is given by $f_{B1}$–aF. Next, individual forces from the time point $t_{B1}$ to the time point $t_{B2}$ are calculated by the calculation unit 11a of the individual force calculation unit 11. The time point $t_{B1}$ to the time point $t_{B2}$, as shown in FIG. 12C, show states in which the operator 6 manipulates the slave robot 26 to gradually strongly bring the forceps 2a into press contact with the internal organ 5. Reference information to calculate the individual forces from the time points $t_{B1}$ to $t_{B2}$ in the calculation unit 11a of the individual force calculation unit 11 is selected by the reference information selecting unit 16 as the time points $t_0$ to $t_1$ in FIG. 13A (see step S8 in FIG. 10I). Similarly, a straight line is calculated by a least-square method based on the forces $f_0, f_{01}, f_{02} \ldots, f_1$ in the calculation unit 11a of the individual force calculation unit 11. In this example, since f=aF is satisfied as shown in FIG. 13C, the individual forces at the time point $t_{B1}$ to the time point $t_{B2}$ in FIG. 13B are obtained by subtracting the force aF from the measured force in the calculation unit 11a of the individual force calculation unit 11. In the example, when the force at the time point $t_{B1}$ in FIG. 13B is given by $f_{B1}$, an individual force at the time point $t_{B1}$ is given by $f_{B1}$–aF. Similarly, when a force at the time point $t_{B2}$ is given by $f_{B2}$, an individual force at the time point $t_{B2}$ is given by $f_{B2}$–aF. The individual force calculated by the calculation unit 11a of the individual force calculation unit 11 is output to the database input/output unit 14 together with time and stored in the measurement information database 9.

<<Force Decision Unit 12>>

The force decision unit 12, based on the pieces of information obtained from the database input/output unit 14, the individual force calculation unit 11, and the reference information generating unit 15, decides whether a load is applied to the abdominal wall 3 based on a force generated by the reference information generating unit 15. More specifically, when the force decision unit 12 decides that the force generated by the reference information generating unit 15 is a predetermined second threshold value (threshold value for deciding an abdominal wall load) (for example, 2 N) or more, the force decision unit 12 decides that a load is applied to the abdominal wall 3 based on a force generated by the reference information generating unit 15. Furthermore, when the force decision unit 12 decides that the force calculated by the calculation unit 11a of the individual force calculation unit 11 is a predetermined fourth threshold value (threshold value for deciding an internal organ load) (for example, 2 N) or more, the force decision unit 12 decides that a load is applied to the internal organ 5 based on the force calculated by the calculation unit 11a of the individual force calculation unit 11. A decision result is output from the force decision unit 12 to the decision result notification unit 17 together with the force used in the decision.

<<Decision Result Notification Unit 17>>

Figure 8A:
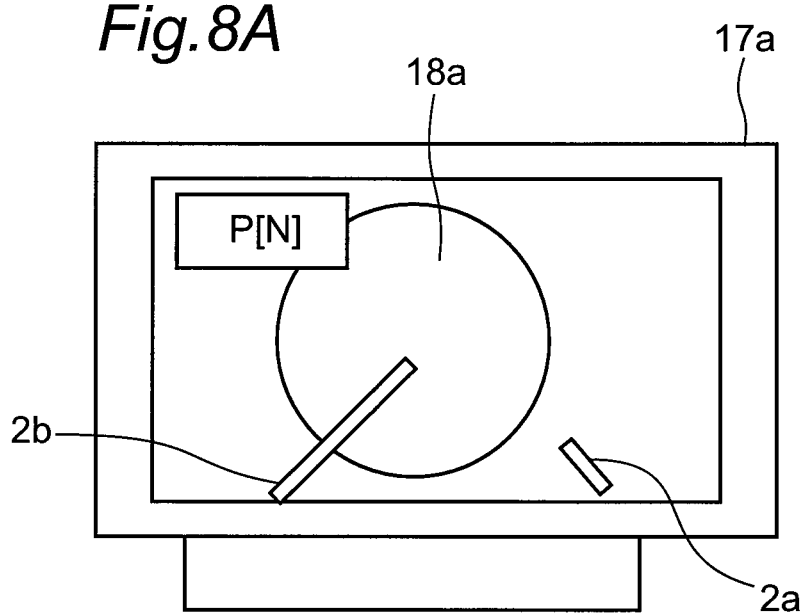
FIG. 8A is a view for describing an example of a decision result notification unit according to the first embodiment of the present invention.
Figure 8B:
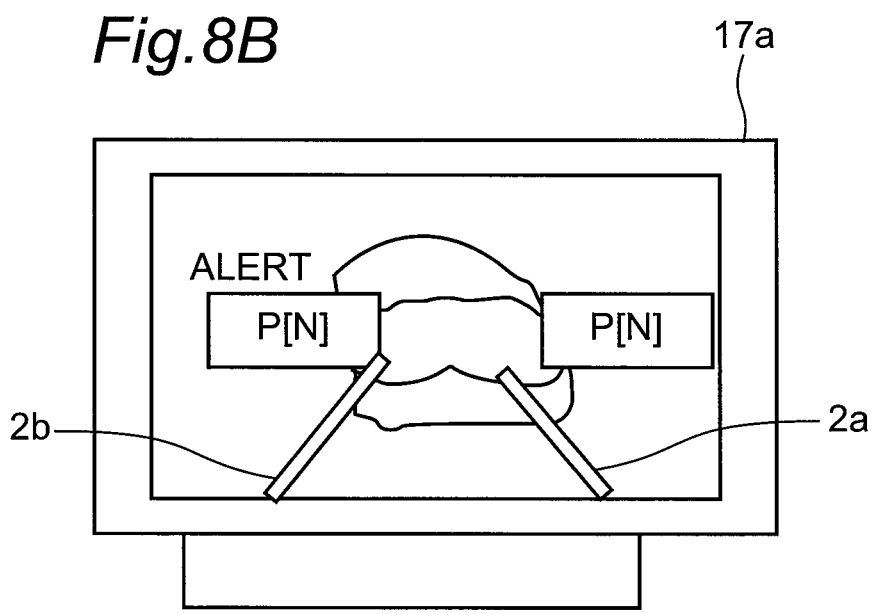
FIG. 8B is a view for describing an example of the decision result notification unit according to the first embodiment of the present invention.

The decision result notification unit 17, based on the information from the force decision unit 12, notifies the operator 6 of a decision result obtained by the force decision unit 12 through a decision result notification device or the like. As the decision result notification device that notifies the operator 6 through the decision result notification unit 17, for example, the monitor 17a, the loudspeaker 17b, or the like can be employed. More specifically, as shown on the monitor 17a in FIG. 8A, when a force acting when the forceps 2a is brought into contact with the trocar 18a is calculated by the reference information generating unit 15 and decided by the force decision unit 12, near a position where the forceps 2a and the trocar 18a are displayed, the force P [N] calculated by the reference information generating unit 15 or an individual force P [N] calculated by the calculation unit 11a of the individual force calculation unit 11 is displayed together with a video image (image) of an endoscope. At this time, when the force decision unit 12 decides that a load is applied to the abdominal wall 3 from the forceps 2a through the trocar 18a, like "ALERT" or the like, a warning (example of a decision result obtained by the force decision unit 12) is displayed by the decision result notification unit 17. More specifically, FIG. 8A shows a view obtained when reference information is generated without the forceps 2a being brought into contact with the internal organ 5. On the other hand, as shown in FIG. 8B, when a force acting when the forceps 2a further moves toward the internal organ 5 and is brought into contact with the internal organ 5 is calculated by the calculation unit 11a of the individual force calculation unit 11, an individual force P [N] calculated by the calculation unit 11a of the individual force calculation unit 11 is displayed together with a video image (image) of an endoscope. At this time, when the force decision unit 12 decides that the forceps 2a applies a load onto internal organ 5, like "ALERT" or the like, a warning (example of a decision result obtained by the force decision unit 12) is displayed by the decision result notification unit 17, and an individual force obtained at this time is displayed by the decision result notification unit 17. When the force decision unit 12 decides that the forceps 2a applies a load, in place of the image display, or in addition to the image display, a warning sound may be made by the loudspeaker 17b, and a warning may be given to the operator 6 by the decision result notification unit 17. The operator 6 may be notified of a magnitude of force by voice.

<<Master-Slave Device 100, Master Robot 25, and Slave Robot 26>>

The master-slave device 100 is a whole device in the first embodiment of the present invention, and a device that can be remotely-manipulated by the operator 6 in the task. The master robot 25 is a robot system to be manipulated such that the operator 6 is in direct contact with the robot system. The slave robot 26 is a robot system that is located at a position distant from the master robot 25 and performs an actual task.

<<Master Mechanism 33 and Slave Mechanism 40>>

A master mechanism 33 is a robot manipulated such that the operator 6 is in direct contact with the robot, and acquires position information (for example, position information from an encoder that detects a rotating angle of a motor for driving each joint portion) obtained at every sample time at which the operator 6 operates the robot, and outputs the position information to a master input/output IF 31.

The slave mechanism 40 is a robot that performs a task to insert the forceps 2a, 2b into the body and operates according to the position information acquired by the master mechanism 33.

<<Timer 43>>

A timer 43 is connected to a master control unit 28 and a slave control unit 35, and, after a predetermined period of time (for example, every 1 msec) has elapsed, executes the master control unit 28 or the slave control unit 35. In FIG. 2, although two timers 43 are disposed, the configuration need not always be used. One timer 43 may be connected to both the master control unit 28 and the slave control unit 35.

<<Master Peripheral Device 30 and Slave Peripheral Device 39>>

A master peripheral device 30 transmits information between the master mechanism 33 and a master control apparatus 29. A slave peripheral device 39 also transmits information between the slave mechanism 40 and a slave control apparatus 34. In this case, the master peripheral device 30 includes the master input/output IF 31 and a master motor driver 32. The slave peripheral device 39 includes a slave input/output IF 37 and a slave motor driver 38.

The master input/output IF 31 receives position information from the master mechanism 33 and outputs the position information to the master control unit 28 of the master control apparatus 29. The position information from the master control unit 28 is output to the master motor driver 32 every predetermined period of time (for example, every 1 msec) through the use of the timer 43 through the master input/output IF 31. The master motor driver 32 receives the position information from the master input/output IF 31 and operates motors (not shown) disposed at joint portions connecting a plurality of links of the master mechanism 33 according to the position information to operate the master mechanism 33. In the joint portion, as in the case of the robot arm, as known by a conventional technique, the motor is controlled by the master motor driver 32 while detecting a rotating angle of the motor by an encoder (not shown).

The slave input/output IF 37 receives the position information from the slave control unit 35 and outputs the position information to the slave motor driver 38 of the slave peripheral device 39. The position information (for example, position information from an encoder that detects a rotating angle of the motor for driving each joint portion) from the slave mechanism 40 is output to the slave control unit 35 every predetermined period of time (for example, every 1 msec) through the use of the timer 43 through the slave input/output IF 37. The slave motor driver 38 receives the position information from the slave input/output IF 37 of the slave peripheral device 39 and operates motors (not shown) disposed at joint portions connecting a plurality of links of the slave mechanism 40 according to the position information to operate the slave mechanism 40. In the joint portion, as in the case of the robot arm, as known by a conventional technique, the motor is controlled by the slave motor driver 38 while detecting a rotating angle of the motor by an encoder (not shown).

<<Master Control Apparatus 29 and Slave Control Apparatus 34>>

The master control apparatus 29 includes the master control unit 28, a force transmitting unit 27, and the timer 43. The master control apparatus 29 has two functions: to output position information of the moved master mechanism 33 to the slave control apparatus 34 every predetermined period of time (for example, every 1 msec) through the use of the timer 43; and to transmit force information input from the slave control apparatus 34 to the operator 6.

When the operator 6 manipulates a master manipulator, i.e., the master mechanism 33 based on the information of the corrected force of the force transmitting unit 27, the master control unit 28 converts the information into electric signals so as to control manipulation information of the master mechanism 33. More specifically, the master control unit 28 outputs the position information of the master mechanism 33 from the master input/output IF 31 to the slave control unit 35 every predetermined period of time (for example, every 1 msec) through the use of the timer 43. The force information from the slave control unit 35 is output to the force transmitting unit 27 through the master control unit 28.

Figure 18:
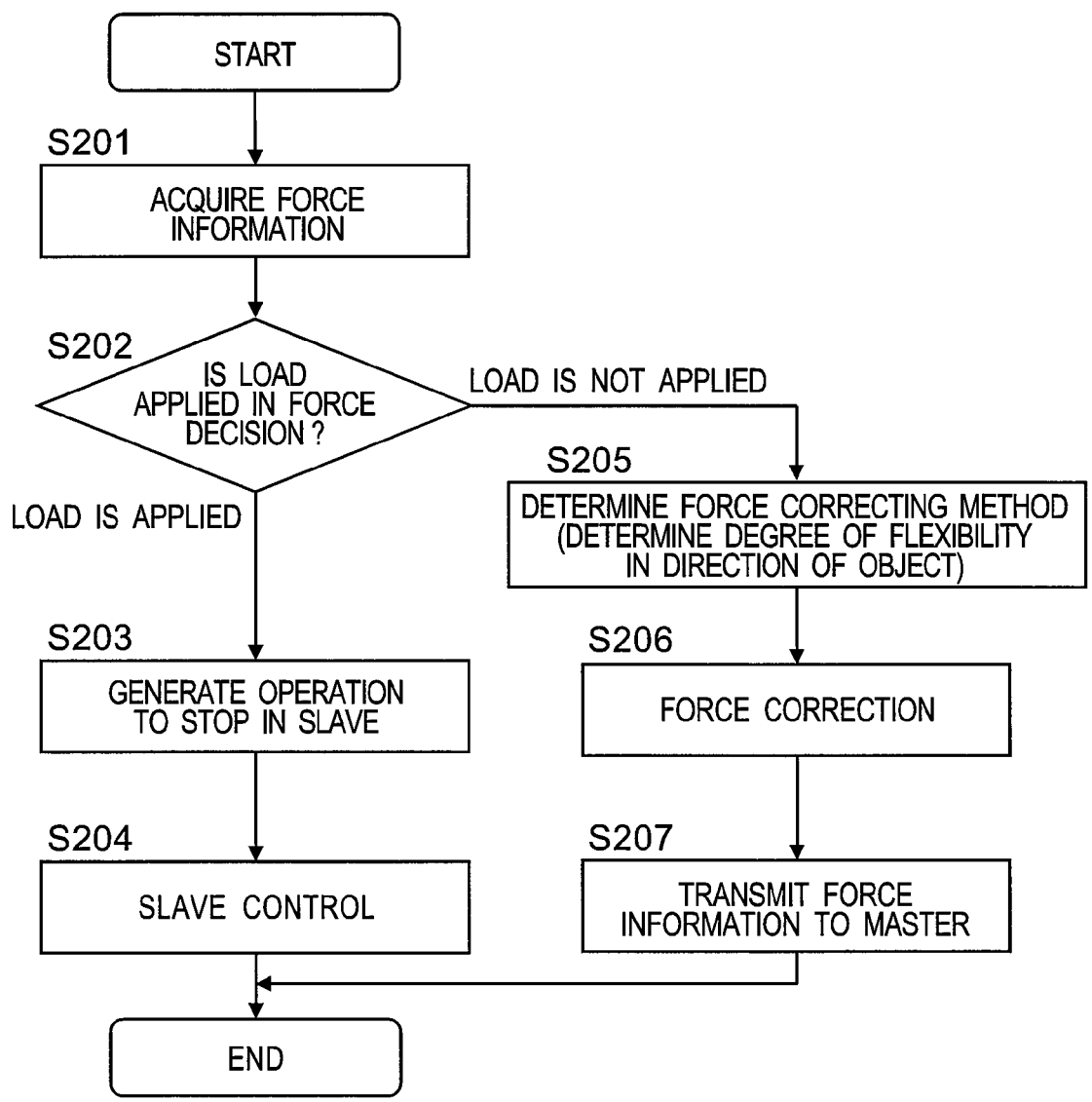
FIG. 18 is a flow chart of the master-slave device according to the second embodiment of the present invention.

The slave control apparatus 34 includes the slave control unit 35, a force correction determination unit 36, the timer 43, and a force correction unit 41. The slave control apparatus 34 has two functions: to cause the slave mechanism 40 to follow the position information from the master control apparatus 29; and to determine a force transmitted to the master control apparatus 29 in a force correction determination unit 36 based on the force information acquired in the force measurement device 1, correct the determined force by the force correction unit 41, and output the corrected force to the master control apparatus 29 as force information. The force measurement devices 1a, 1b, as shown in FIG. 18, are disposed on the tip end sides of the forceps 2a, 2b and outside the body near positions where the slave robot 26 is disposed.

The slave control unit 35 is connected to the slave mechanism 40 through the slave peripheral device 39 and the master control unit 28, and outputs control signals that transmit manipulation information of the master mechanism 33 transmitted from the master control unit 28 to the slave mechanism 40. Based on the control signals transmitted from the slave control unit 35, the slave mechanism 40 is manipulated to perform a slave operation.

<<Force Transmitting Unit 27>>

The force transmitting unit 27 transmits the information of the force after corrected by the force correction unit 41 (will be described later) to the master mechanism 33, resulting in transmitting the information to the operator 6. More specifically, the force transmitting unit 27 force-controls the slave mechanism 40 through the slave control unit 35 by using the force information from the slave control unit 35 as a desired value to transmit the information to a hand of the operator 6. As a direction in which a force is generated, one axis in the insertion direction of the master mechanism 33 is used. However, 3 axes of the insertion direction and directions perpendicular thereto may be used.

<<Force Correction Determination Unit 36>>

A force correction determination unit 36 determines information relating to a force correcting method based on the force information input from the force measurement device 1a, 1b to the force correction determination unit 36, and outputs the information relating to the determined force correcting method together with the force information from the force correction determination unit 36 to the slave control unit 35. More specifically, the force correction determination unit 36 determines, out of the force information detected by the force measurement device 1a, 1b, information relating to a correction part serving as information representing a specific force detection part to be corrected, a type of a force corrected by the force correction unit 41, and a correcting method in the force correction unit 41 (will be described later), as information relating to a force correcting method.

The type of the force to be corrected by the force correction unit 41 means use of either an individual force measured by the force measurement device 1a or 1b or the force of the force detection unit 13.

A method of detecting a force detection part will be described with reference to FIGS. 9A and 9B. FIG. 9A is a graph showing a relationship between the force detected by the force measurement device 1a or 1b disposed in the slave mechanism 40 and time. This example shows information of a force detected by the force detection unit 13 in the force measurement device 1a or 1b.

FIG. 9B is a graph showing a relationship between a force transmitted to the master mechanism 33 and time, and shows force information transmitted to the master mechanism 33 after the force information is corrected by the force correction unit 41 (will be described later). In this drawing, a solid line and white circles indicate values obtained before correction, and a broken line and black circles indicate corrected values.

Based on pieces of force information (for example, force information ($f_{11}$) and force information ($f_{12}$) in FIG. 9A) acquired every predetermined period of time in the force measurement device 1a or 1b, the force correction determination unit 36 determines whether a displacement of the pieces of force information (difference of the pieces of force information, i.e., ($f_{12}$)−($f_{11}$) in FIG. 9A) exceeds a threshold value (threshold value for determining displacement) (for example, 1.0 N) of the displacement of the pieces of force information.

If the force correction determination unit 36 determines that ($f_{12}$)−($f_{11}$) in FIG. 9A exceeds the threshold value of the displacement of the pieces of force information (threshold value for determining displacement) (for example, 1.0 N), the force correction determination unit 36 determines "correction" to detect that the forceps 2a or 2b gripped by the slave mechanism 40 collides with the abdominal wall 3 or the internal organ 5 or that a strong force acts from the forceps 2a or 2b onto the abdominal wall 3 or the internal organ 5. However, "the displacement exceeds the threshold value" means that the threshold value has the same sign as that of the threshold value and that the absolute value of the displacement is larger than the threshold value. In this case, the "correction" means that correction is performed by the force correction unit 41.

On the other hand, when the force correction determination unit 36 determines that the displacement (($f_{12}$)−($f_{11}$)) of the pieces of force information does not exceed the threshold value (threshold value for determining displacement) of the displacement of the pieces of force information, the force correction determination unit 36 detects "no correction". In this case, the "no correction" means that correction is not performed by the force correction unit 41.

The force correction determination unit 36 sets a time point at which the displacement (($f_{12}$)−($f_{11}$)) of the pieces of force information acquired by the force measurement device 1a or 1b exceeds the threshold value (threshold value for determining displacement), as "force correction start time" (correction start time) (time point A1 in FIG. 9A). The force correction determination unit 36 sets a time point at which a displacement (($f_{14}$)−($f_{13}$)) of pieces of force information acquired by a force information acquiring unit 26 is the threshold value (threshold value for determining displacement) or less, as "force correction end time" (correction end time) (time point C1 in FIG. 9A). Thus, a section from the correction start time to the correction end time corresponds to a force correction part (correction part) at which force correction is performed.

In this example, although the section in which correction should be performed by using a displacement of force is detected by the force correction determination unit 36, a section (force correction part or correction part) by using a displacement of velocity or both the displacements of velocity and force may be detected by the force correction determination unit 36.

A correcting method performed in the force correction unit 41 (will be described later) is determined by the force correction determination unit 36.

Firstly, a type of a force to be corrected by the force correction unit 41 is determined by the force correction determination unit 36. More specifically, either an individual force measured by the force measurement device 1a or 1b or the force of the force detection unit 13 is determined by the force correction determination unit 36. The force correction determination unit 36, based on a determination flag held therein, determines a force that should be transmitted to the master control apparatus 29 from the individual force determined by the force correction determination unit 36 or the force of the force detection unit 13. As the determination flag set in the force correction determination unit 36, "0" is set when the force of the force detection unit 13 is transmitted, and "1" is set when the individual force of the force measurement device 1a or 1b is transmitted.

Secondly, a constant "k" to correct a force by the force correction unit 41 is determined by the force correction determination unit 36. The force correction determination unit 36 determines the constant "k" based on a degree of flexibility "s" of an object such as the forceps 2a or 2b or an endoscope or an object to be treated such as a trocar 18 or the internal organ 5, and a type "f" of a force measured by the force measurement device 1a or 1b.

The degree of flexibility "s", as an example, is expressed by an elastic coefficient of an object or an object to be treated. When the degree decreases, the object or the object to be treated becomes soft, and when the degree increases, the object or the object to be treated becomes hard. For example, since a normal region and an affected area of a liver and a born have different flexibilities and regions have different flexibilities, the degree of flexibility "s" (degree of flexibility) may be determined by the force correction determination unit 36 together with three-dimensional position information of an internal organ.

The type "f" of the force measured by the force measurement device 1a or 1b represents a type of either the individual force measured by the force measurement device 1a or 1b or the force of the force detection unit 13 that is should be transmitted. The type "f" of force is set to "2" when the force of the force detection unit 13 is exhibited, and the type "f" of force is set to "1" when the individual force is exhibited.

Thus, the constant "k" is calculated by the force correction determination unit 36 according to an equation: constant k=1/(a×s+b×f). Note that "a" and "b" are constants that are set to cause the force correction determination unit 36 to make a value of (a×s+b×f) "1" or more.

Thirdly, correcting method performed in the force correction unit 41 will be described below. As the correcting method, as an example, two methods, i.e., a first "method A" (a solid line in FIG. 9C denotes force information obtained before correction, and a broken line denotes corrected force information) in which the entire correction section calculated as described above is corrected according to an equation: $f_{new}=f_{12}-k\times((f_{12})-(f_{11}))$ and a second "method B" (FIG. 9B) in which a value is calculated by the force correction determination unit 36 according to $f_{new}=f_{12}-k\times((f_{12})-(f_{11}))$ until the force increases and the calculated value is extended after a timing at which the force decreases until a correction end section are given. More specifically, the "method A" is a method that performs correction such that an absolute value of force information at a force correction part is reduced by a predetermined correction amount. More specifically, the "method B" is a method that performs correction such that the reduction of the absolute value of force information at the force correction part by the predetermined correction amount is maintained for a predetermined period of time. The correction is performed by the force correction unit 41 using either the "method A" or the "method B". In this case, an expression of "absolute value of force information" is used to correct a force to weaken the force regardless of the sign of force. When the force is positive, the force becomes weak when the force is reduced by a predetermined correction amount. When the force is negative, the force does not become weak until the force is increased by a predetermined correction amount. When the equation: $f_{new}=f_{12}-k\times((f_{12})-(f_{11}))$ is used, a calculation is performed to reduce an absolute value of $f_{new}$. Note that, since the equation: constant $k=1/(a\times s+b\times f)$ defines the value of $(a\times s+b\times f)$ as 1 or more, the value must be positive. A method to be used is determined by the force correction determination unit 36 in advance or determined by the force correction determination unit 36 based on the value of the previously determined constant k. For example, when the force correction determination unit 36 determines that the constant "k" is smaller than a predetermined value (threshold value for determining correcting method) (for example, less than 0.2) (in other words, a correction amount is less than a predetermined threshold value), as shown in FIG. 9C, the "method A" is determined. When the force correction determination unit 36 determines that the constant "k" is equal to or larger than the predetermined value (threshold value for determining correcting method) (in other words, a correction amount is equal to or larger than a predetermined threshold value), as shown in FIG. 9C, the "method B" is determined. When the force correction determination unit 36 determines that the constant "k" is smaller than the predetermined threshold value, a difference between $f_{new}$ and $f_{12}$ is small. For this reason, a person can sufficiently feel the force even though transmission is not performed by extending the time point $f_{12}$, the force correction determination unit 36 can determine the "method A". When $f_{new}$ is calculated, the force correction determination unit 36 must set the constant "k" within a range in which an absolute value of $k\times((f_{12})-(f_{11}))$ does not exceed an absolute value of $f_{12}$.

The information relating to the section to be corrected, the correcting methods determined as the above first, second, and third steps, and information relating to the force measured by the force measurement device 1a or 1b are output from the force correction determination unit 36 to the force correction unit 41.

<<Force Correction Unit 41>>

The force correction unit 41 corrects the force information at the correction part by the correcting method according to the correction part and the correcting method determined by the force correction determination unit 36, resulting in correcting a force that should be transmitted to the master mechanism 33, by the force transmitting unit 27.

More specifically, when the force correction determination unit 36 determines "no correction" at the force correction part, the force correction unit 41 outputs the force detected by the force measurement device 1a or 1b to the slave control unit 35 through the force correction determination unit 36 without correcting the force. When the force correction determination unit 36 determines "correction" at the force correction part and "force correction start time", the force correction unit 41 corrects the force detected by the force measurement device 1a or 1b and outputs the corrected information to the slave control unit 35 through the force correction determination unit 36. More specifically, as a type of a force to be corrected, the force correction determination unit 36 determines either an individual force measured by the force measurement device 1a or 1b or the force of the force detection unit 13.

Based on the force, the correcting method ("method A" or "method B"), and the constant "k" determined by the force correction determination unit 36, correction is performed by the force correction unit 41.

More specifically, when the force correction determination unit 36 determines the "method A", as shown in FIG. 9C, the entire correction section is corrected by the force correction unit 41 according to the equation: $f_{new}=f_{12}-k\times((f_{12})-(f_{11}))$.

When the force correction determination unit 36 determines the "method B", as shown in FIG. 9B, with respect to a displacement $((f_{12})-(f_{11}))$ in FIG. 9A) of force information at the force correction start time point (time point A1 in FIG. 9A), the constant "k" (for example, 0.5) is set and $f_{new}=f_{12}-k\times((f_{12})-(f_{1}))$ is satisfied to perform correction in the force correction unit 41.

Subsequently, until a time point B1, the correction is sequentially performed by the force correction unit 41 through the same method as described above. The time point B1 is a time point at which the force takes a downward turn from an upward side.

Next, in a period from the time point B1 to a correction end time point (time point C1 in FIG. 9A), the force calculated at the time point B1 is used by the force correction unit 41. At the force correction end time (time point C1 in FIG. 9A), the correction by the force correction unit 41 is ended. When the force calculated at the time point B1 is transmitted from the force correction unit 41 to the master mechanism 33 for a relatively long time in a period from the time point B1 to the force correction end time point (time point C1 in FIG. 9A), even though the force is corrected to be smallish by the force correction unit 41, an operator can be prevented from being difficult to feel the force.

Figure 14:
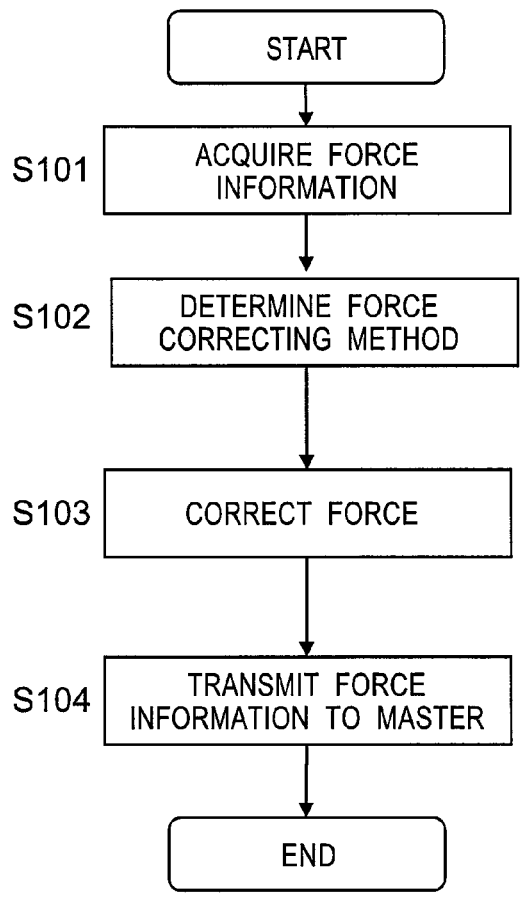
FIG. 14 is a flow chart of a master-slave device according to the first embodiment of the present invention.

A manipulation procedure of the master-slave device 100 according to the first embodiment will be described below with reference to the flow chart in FIG. 14. In FIG. 14, a description will be given of a transmission procedure of a force generated when the operator 6 directly manipulates the master mechanism 33 to operate the slave mechanism 40 so as to bring the forceps 2a, 2b into contact with the internal organ 5.

In step S101, when the forceps 2a or 2b is brought into contact with the abdominal wall 3 or the internal organ 5, force information is detected by the force measurement device 1a or 1b and the force detection unit 13 (see step S2 and steps S6 to S9), and the force information is output from the force measurement device 1a or 1b and the force detection unit 13 to the force correction determination unit 36.

Next, in step S102, in the force correction determination unit 36, more specifically, out of the pieces of force information detected by the force measurement device 1a or 1b, information relating to a correction part and serving as information representing a part where correction is performed, a type of a force to be corrected by the force correction unit 41, the constant "k" to correct the force in the force correction unit 41, and a correcting method used to correct a force in the force correction unit 41 are determined. The correcting method determined by the force correction determination unit 36 is output from the force correction determination unit 36 to the force correction unit 41 together with the information of the force.

Next, in step S103, based on the correcting method determined by the force correction determination unit 36, the force correction unit 41 corrects the force. The force correction unit 41 outputs the corrected information to the slave control unit 35 through the force correction determination unit 36. When the force correction determination unit 36 determines "no correction" at the force correction part, the force correction unit 41 directly outputs the force detected by the force measurement device 1a or 1b to the slave control unit 35 through the force correction determination unit 36 without causing the force correction unit 41 to correct the force detected by the force measurement device 1a or 1b.

Next, in step S104, the force information output from the force correction unit 41 to the slave control unit 35 is sent from the slave control unit 35 to the master control unit 28 and transmitted to the force transmitting unit 27. The force information input to the force transmitting unit 27 is transmitted to a hand of the operator 6.

Effects of First Embodiment

As described above, in the first embodiment, even though the slave mechanism 40 of the slave robot 26 and the master mechanism 33 of the master robot 25 have different inertia forces, the force correction determination unit 36 determines a correcting method for the force information to correct the force information in the force correction unit 41, and the master control unit 28 and the slave control unit 35 control the master-slave robot based on the corrected force information. As a result, the master mechanism 33 can be prevented from being largely moved due to application of large force to the master mechanism 33, and the operator 6 can feel the feedback force when the correction is performed to prevent the master mechanism 33 from being largely moved.

Second Embodiment

Figure 15:
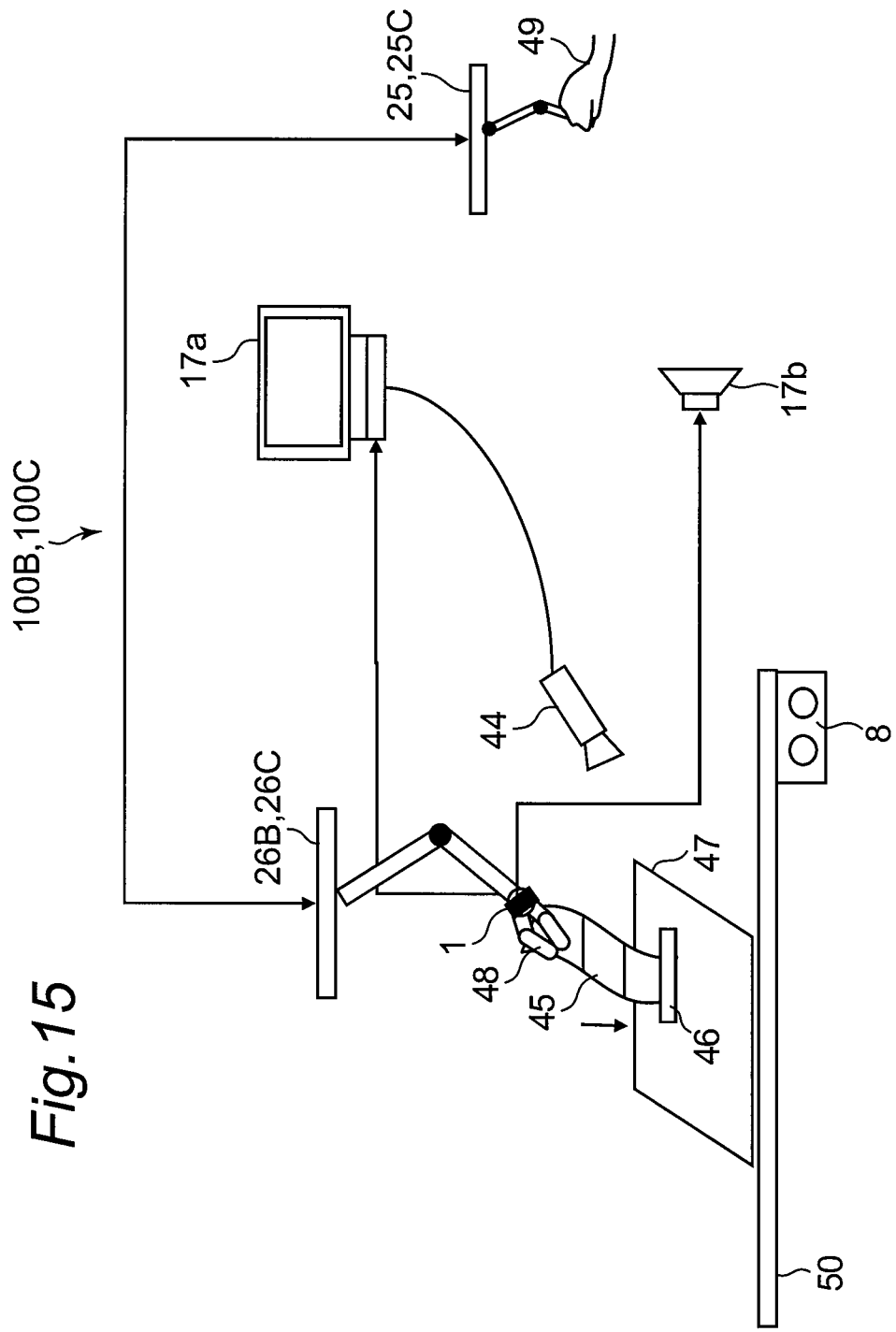
FIG. 15 is a view showing an outline of a configuration of a master-slave device according to the second embodiment of the present invention.
Figure 16A:
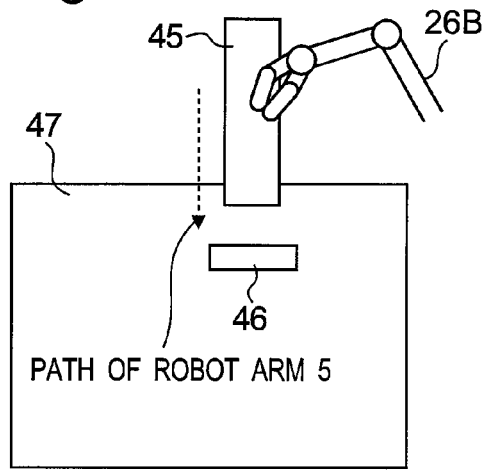
FIG. 16A is a view for describing a manipulation of flexible substrate insertion in the second embodiment of the present invention.
Figure 16B:
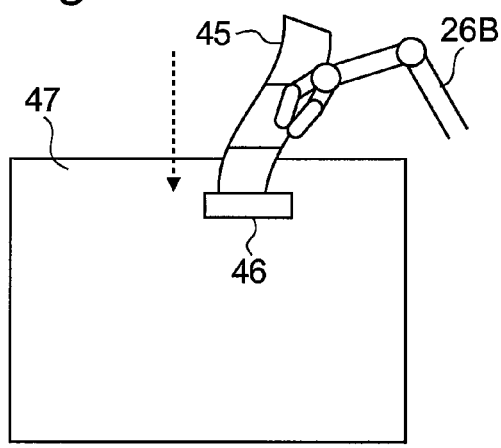
FIG. 16B is a view for describing a manipulation of flexible substrate insertion in the second embodiment of the present invention.
Figure 16C:
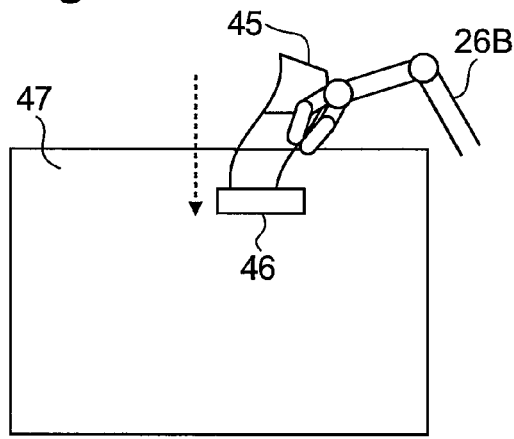
FIG. 16C is a view for describing a manipulation of flexible substrate insertion in the second embodiment of the present invention.
Figure 16D:
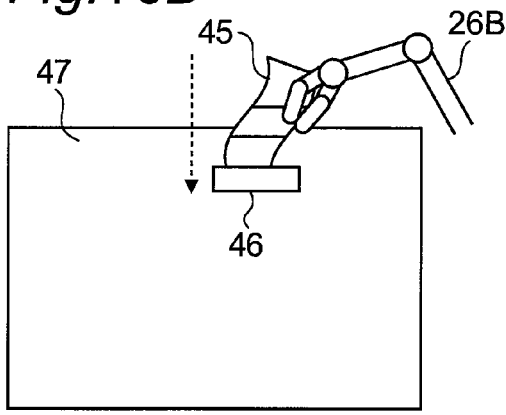
FIG. 16D is a view for describing a manipulation of flexible substrate insertion in the second embodiment of the present invention.
Figure 16E:
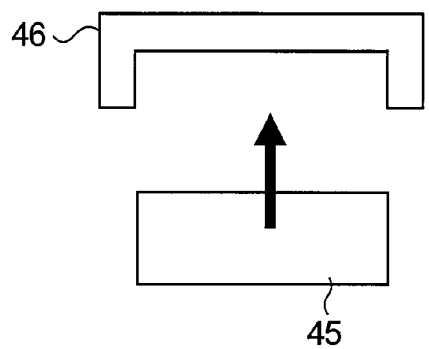
FIG. 16E is a plan view of a periphery of a flexible substrate insertion hole, describing the manipulation of flexible substrate insertion, corresponding to FIG. 16A, in the second embodiment of the present invention.
Figure 16F:
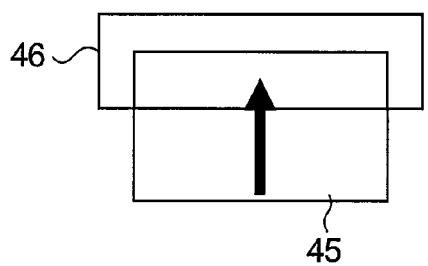
FIG. 16F is a plan view of the periphery of the flexible substrate insertion hole, describing the manipulation of flexible substrate insertion, corresponding to FIG. 16B, in the second embodiment of the present invention.
Figure 16G:
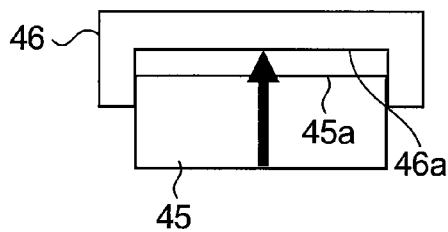
FIG. 16G is a plan view of the periphery of the flexible substrate insertion hole, describing the manipulation of flexible substrate insertion, corresponding to FIG. 16C, in the second embodiment of the present invention.

In a second embodiment, as shown in FIG. 15, as an example, a description will be given of a case in which an inserting task of a flexible substrate 45 is performed by using a master-slave device (master-slave robot) 100B. A portion obtained by removing the slave mechanism 40 and the master mechanism 33 from the master-slave device 100B is also called a control apparatus for a master-slave robot.

Firstly, an outline of the master-slave device 100B according to the second embodiment of the present invention will be described below.

As shown in FIG. 15, as an example, in a cell production in a factory, a teaching of a task that attaches the flexible substrate 45 to an insertion hole 46 of a printed board 47 for a device such as a television set, a DVD recorder, or a mobile phone will be described.

Thus, the master-slave device 100B includes the slave mechanism 40 having a slave robot 26B that grips a flexible substrate 45 serving as an example of an object by a hand 48 and performs a task while being in touch with an insertion hole 75 of the printed board 47 for the device serving as an example of an object to be treated, and the master mechanism 33 having the master robot 25 that causes a worker 49 to remotely-manipulate the slave mechanism 40.

The slave robot 26B of the master-slave device 100B is a robot that is disposed on an upper part or a wall surface of a work table 50 in which the printed board 47 for the device is installed, and performs a task that inserts the flexible substrate 45 into the insertion hole 46 of the printed board 47 for the device.

The input IF 8 such as a console panel on which buttons are disposed is disposed on the side surface of the work table 50.

A hand 48 that grips the flexible substrate 45 is attached to a tip end of the slave robot 26B.

An image-pickup device 44 such as a camera is disposed on the side surface of the work table 50 and takes an image of the flexible substrate 45 or the insertion hole 46.

A force measurement device 1 is disposed at a wrist portion of the hand 48 and measures a force generated when the flexible substrate 45 acts on the printed board 47 or the insertion hole 46.

When the worker 49 manipulates the master robot 25 while checking a video image taken by the image-pickup device 44 with the monitor 17a, the slave robot 26B operates. When the force measured by the force measurement device 1 is fed back from the slave robot 26B to the master robot 25, the worker 49 can teach the slave robot 26B with a manipulation feeling as if the worker directly manipulates the flexible substrate 45. Based on an operational information generated by teaching, the slave robot 26B is automatically operated.

An outline of a manipulation procedure of the master-slave device 100B will be described.

The worker 49 powers on the device by using the input IF 8 disposed on the side surface of the work table 50.

When the worker 49 manipulates the master robot 25, the slave robot 26B operates by moving based on a force applied by the worker 49. More specifically, as shown in FIGS. 16A to 16H, when the master robot 25 is manipulated, the slave robot 26B inserts the flexible substrate 45 into the insertion hole 46.

Figure 19:
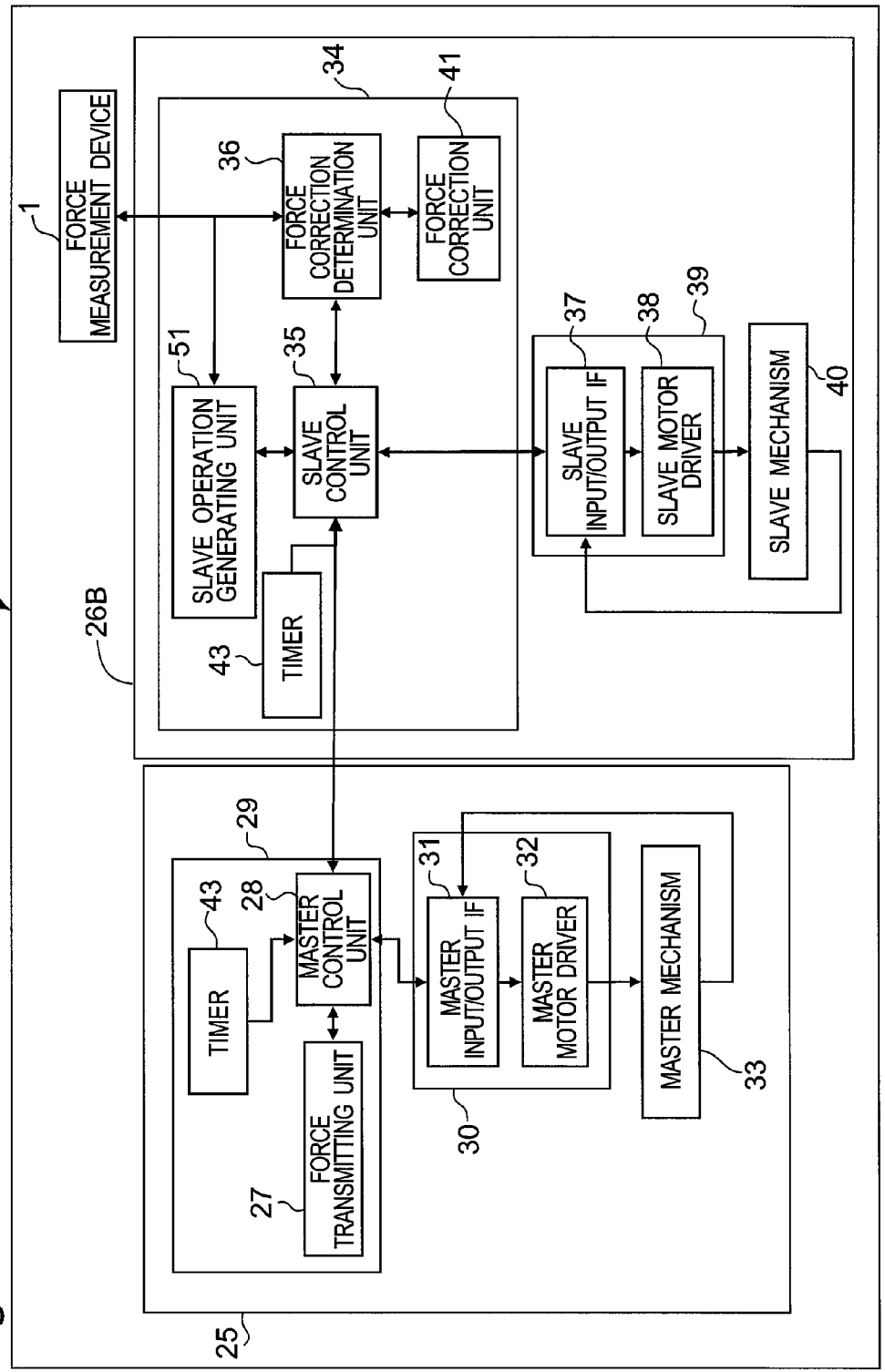
FIG. 19 is a block diagram showing a detailed configuration of the master-slave device according to the second embodiment of the present invention.

FIG. 19 shows configurations of the master robot 25, the slave robot 26B, and the force measurement device 1 in the second embodiment. The descriptions of the portions common in the first and second embodiments are omitted, and only different portions will be described below.

<<Force Measurement Device 1>>

The force measurement device 1 has the same functions as those in the first embodiment, is disposed at the wrist portion of the hand 48, and individually measures a force generated when the flexible substrate 45 acts on the printed board 47 or the insertion hole 46 or a force acting on the tip end of the flexible substrate 45. The force measurement device 1 serves as one example of a force information acquiring unit, and includes at least the force detection unit 13, the reference information generating unit 15, and the individual force calculation unit 11.

From the force measurement device 1, an output value from the force detection unit 13, an individual force detected by the individual force detection unit 11, and a decision result obtained in the force decision unit 12 are output to the force correction determination unit 36 as in the first embodiment. The force measurement device 1 includes the same configuration as that of the force measurement device 1 in the first embodiment.

<<Force Detection Unit 13>>

The force detection unit 13 has the same functions as those in the first embodiment and detects a force generated when the flexible substrate 45 is brought into contact with the insertion hole 46, the printed board 47, or the like. The force detection unit 13 may have the same configuration as that of the force detection unit 13 of the first embodiment.

<<Instrument Position Detection Unit 19>>

The instrument position detection unit 19 has the same functions as those in the first embodiment and detects a tip end position, on an opposite side of the insertion hole 46, of the flexible substrate 45 serving as an example of an instrument. The instrument position detection unit 19, as in the first embodiment, may calculate the tip end position with a magnetic position measurement sensor to detect the position, or may detect a hand position of the slave robot 26B that grips the flexible substrate 45, as the tip end position. The hand position of the slave robot 26B is output by a slave input/output IF.

<<Reference Information Generating Unit 15>>

The reference information generating unit 15 has the same functions as those in the first embodiment and generates reference information serving as information configured by pairing a position of the flexible substrate 45 detected by the instrument position detection unit 19 before the flexible substrate 45 passes through the insertion hole 46 and is brought into contact with the bottom of the insertion hole 46, a value detected by the force detection unit 13, and a basing point calculated by a method (will be described later). The reference information generating operation is the same as that in the first embodiment. In this case, the substrate is inserted into the insertion hole, the substrate is tilted with respect to the insertion hole without bring the tip end of the substrate into contact with the bottom of the insertion hole, and the reference information is generated.

—Reference Information Database 22—

The reference information database 22, as in the first embodiment, stores reference information serving as information configured by pairing information relating to a force detected by the force detection unit 13, a position of the flexible substrate 45 detected by the instrument position detection unit 19, and a basing point calculated by the reference information generating unit 15 together with time through the database input/output unit 14 through the use of the timer 10. More specifically, out of the reference information, the information relating to the force detected by the force detection unit 13, the position of the flexible substrate 45 detected by the instrument position detection unit 19 before the flexible substrate 45 passes through the insertion hole 46 of the flexible substrate 45 and is brought into contact with the bottom of the insertion hole 46, and the basing point calculated by the reference information generating unit 15 are generated by the reference information generating unit 15 every predetermined period of time (for example, every 4 msec) through the use of the timer 10, are output from the reference information generating unit 15 to the database input/output unit 14 together with time, and are stored in the reference information database 22.

—Measurement Information Database 9—

The information relating to the force detected by the force detection unit 13 and the positions of the flexible substrate 45 detected by the instrument position detection unit 19 before and after the flexible substrate 45 is brought into contact with the bottom of the insertion hole 46 are generated by the measurement information generating unit 15 through the database input/output unit 14 every predetermined period of time (for example, every 4 msec) through the use of the timer 10, are output from the measurement information generating unit 15 to the database input/output unit 14 together with time, and are stored in the measurement information database 9 as measurement information.

<<Individual Force Calculation Unit 11>>

The calculation unit 11a of the individual force calculation unit 11 has the same functions as those in the first embodiment and calculates an individual force generated when the flexible substrate 45 is brought into contact with the bottom of the insertion hole 46 based on the reference information stored in the reference information database 22 and the force detected by the force detection unit 13, through the database input/output unit 14. The reference information used by the reference information selecting unit 16 of the individual force calculation unit 11 is selected by the reference information selecting unit 16 from the reference information read by the database input/output unit 14 from the reference information database 22 based on a present position (force measurement state) of the flexible substrate 45.

The reference information selecting unit 16 selects reference information closest to the present (force measurement state) position of the flexible substrate 45 (however, a position of an axis orthogonal to an insertion direction except for a position in the insertion direction) from positions of the flexible substrate 45 obtained before the flexible substrate 45 passes through the insertion hole 46 and is brought into contact with a bottom 46a of the insertion hole 46. The ID of the reference information selected by the reference information selecting unit 16 is stored from the reference information selecting unit 16 as an "ID of reference information" of the measurement information database 9 through the database input/output unit 14.

The individual force calculation unit 11 detects individual forces acting when the flexible substrate 45 is brought into contact with a bottom 46a of the insertion hole based on the reference information selected by the reference information selecting unit 16. More specifically, based on the reference information read from the reference information database 22 by the database input/output unit 14, the reference information selecting unit 16 selects reference information at a time point at which the force is desired to be measured. Next, a value obtained by subtracting a value of a force of the reference information selected by the reference information selecting unit 16 from the value of the force detection unit 13 at the time point is calculated by the calculation unit 11a of the individual force calculation unit 11, as an individual force. The individual force calculated by the calculation unit 11a of the individual force calculation unit 11 is stored from the calculation unit 11a of the individual force calculation unit 11 into the measurement information database 9 through the database input/output unit 14.

<<Force Decision Unit 12>>

The force decision unit 12, based on the pieces of information obtained from the database input/output unit 14, the individual force calculation unit 11, and the reference information generating unit 15, decides whether a load is applied to the flexible substrate 45 or the insertion hole 46 based on a force generated by the reference information generating unit 15. More specifically, when the force decision unit 12 decides that the force generated by the reference information generating unit 15 is the predetermined second threshold value (threshold value for deciding a load on the flexible substrate or the insertion hole) (for example, 2 N) or more, the force decision unit 12 decides that a load is applied to the flexible substrate 45 or the insertion hole 46 based on the force generated by the reference information generating unit 15.

<<Decision result Notification Unit 17>>

The decision result notification unit 17, based on the information from the force decision unit 12, notifies the worker 49 of a decision result obtained by the force decision unit 12 through a decision result notification device or the like. As the decision result notification device that notifies the worker 49 through the decision result notification unit 17, for example, the monitor 17a, the loudspeaker 17b, or the like can be employed.

<<Master Mechanism 33 and Slave Mechanism 40>>

The master mechanism 33 is a robot manipulated such that the worker 49 is in direct contact with the robot, acquires position information obtained at every sample time when the worker 49 operates the robot, and outputs the position information to the master input/output IF 31.

The slave mechanism 40 is a robot that performs a task to insert the flexible substrate 45 into the insertion hole 46 and operates according to the position information acquired by the master mechanism 33.

<<Force Correction Determination Unit 36>>

The force correction determination unit 36 determines information relating to a force correcting method based on the force information input from the force measurement device 1 to the force correction determination unit 36 and outputs information relating to the determined force correcting method together with the force information from the force correction determination unit 36 to the slave control unit 35. More specifically, the force correction determination unit 36 determines, out of the force information detected by the force measurement device 1, information relating to a correction part serving as information representing a specific force detection part to be corrected, a type of a force corrected by the force correction unit 41, and a correcting method in the force correction unit 41 (will be described later), as information relating to a force correcting method.

Firstly, a type of a force to be corrected by the force correction unit 41 is determined by the force correction determination unit 36. The type is determined by the force correction determination unit 36 using the same method as that in the first embodiment.

Secondly, a constant "k" to correct a force by the force correction unit 41 is determined by the force correction determination unit 36. The constant "k" is determined by the force correction determination unit 36 based on a degree of flexibility "s" of an object such as the flexible substrate 45 or an object to be treated such as the insertion hole 46 or the printed board 47 and the type "f" of a force measured by the force measurement device 1. This means that the force correction determination unit 36 determines a correction amount set when an absolute value of force information at a force correction part is reduced based on at least one piece of information of the type of either the individual force measured by the force measurement device 1 or the force of the force detection unit 13 and information of the degree of flexibility "s".

The flexible substrate 45 structurally has a flexible direction and an inflexible direction. In a z direction or a y direction shown in FIG. 17, the flexible substrate 45 is easily bent with the force being applied in any direction of positive and negative directions. On the other hand, in an x direction, the flexible substrate 45 is not easily bent with the force being applied. In this case, by the force correction determination unit 36, the degree of flexibility "s" is set to a small value in a direction in which the flexible substrate 45 is easily bent, and is set to a large value in a direction in which the flexible substrate 45 is not easily bent. This means that, by the force correction determination unit 36, in a plurality of directions including a task direction of an object or an object to be treated and directions intersecting with the task direction, a correction amount is determined to be small when the flexibility is high (bending is easy, and the degree of flexibility "s" is reduced). For example, the force detection unit 13 that can detect 6 axes is included, the degrees of flexibility "s" may be independently set in the six axes, respectively.

Furthermore, as in the first embodiment, the type "f" of force is set to "2" when the force of the force detection unit 13 is exhibited, and the type "f" of force is set to "1" when the individual force is exhibited.

In addition, the constant "k" is calculated by the force correction determination unit 36 according to an equation: constant k=1/(a×s+b×f). Note that "a" and "b" are constants. This means that when the constant "k" is calculated as described above, as a result, the force correction determination unit 36 determines correction such that a correction amount set when the type "f" of the force determined by the force correction determination unit 36 is determined as the force individually acting on the object to be treated by the object is larger than a correction amount set when the type of the force is determined as the information of the force acquired by the force detection unit 13.

Thirdly, a correcting method used in correction of the force correction unit 41 is determined by the same method as that in the first embodiment.

<<Force Correction Unit 41>>

The force correction unit 41, as in the first embodiment, corrects a force that should be transmitted to the master mechanism 33 by the force transmitting unit 27 according to the correction part and a correcting method that are determined by the force correction determination unit 36.

For example, when the force correction determination unit 36 determines "no correction" at the force correction part, the force correction unit 41 outputs the force detected by the force measurement device 1 to the slave control unit 35 through the force correction determination unit 36 without correcting the force.

For example, when the force correction determination unit 36 determines "correction" at the force correction part, the force correction unit 41 calculates a value obtained by correcting the force information measured by the force measurement device 1, as a force bed back to the master robot 25.

<<Slave Operation Generating Unit 51>>

A slave operation generating unit 51, while teaching the master robot 25, based on force information acquired by the force measurement device 1 and a decision result of a load, for example, stops a slave operation when a load equal to or larger than a predetermined load is applied to an object or an object to be treated (flexible substrate 45 or insertion hole 46), or, based on position information of the measurement information database 9 recorded after the master robot 25 is taught, generates an operation to automatically operate the slave robot 26B. When the position information of the measurement information database 9 is output from the slave operation generating unit 51 to the slave control unit 35 every predetermined period of time, the slave control unit 35 can automatically operate the slave robot 26B. Furthermore, when a force presented by the master robot 25 is corrected by the force correction unit 41, when there is a portion where a position fluctuates before and after the correction, in the slave operation generating unit 51, the operation is corrected such that smoothing is performed by using a low-pass filter included in the slave operation generating unit 51. In this case, whether there is a portion where a position fluctuates before and after the correction is decided as described below as an example. A case in which a sign (positive or negative) of a displacement of position information acquired every predetermined period of time (for example, $t_1$) changes from the sign of the previous displacement is set to "1", and a case in which the sign does not change is set to "0". A case in which the number of times when the sign changes every predetermined period of time (for example, time $t_2$, longer than time $t_1$. More specifically, a period of time including 6 times $t_1$) is a predetermined threshold value or more (for example, 3) is decided as a "fluctuating part".

Next, a manipulation procedure of the master-slave device 100B according to the second embodiment will be described below with reference to the flow chart in FIG. 18. In FIG. 18, a description will be given of a transmission procedure of a force generated when the worker 49 directly manipulates the master mechanism 33 to operate the slave mechanism 40 so as to bring the flexible substrate 45 into contact with the insertion hole 46.

Firstly, in step S201, when the flexible substrate 45 is brought into contact with the insertion hole 46, force information is detected by the force measurement device 1 and the force detection unit 13 and is output from the force measurement device 1 and the force detection unit 13 to the force correction determination unit 36.

Next, in step S202, the force decision unit 12 decides whether a load is applied to the flexible substrate 45 or the insertion hole 46. When the force decision unit 12 decides that the load is applied, in step S203, the slave operation generating unit 51 generates an operation to stop the operation, and, in step S204, the slave mechanism 40 is controlled by a command from the slave operation generating unit 51. In step S202, the force decision unit 12 decides that no load is applied, the process proceeds to step S205.

In step S205, in the force correction determination unit 36, more specifically, of the pieces of force information detected by the force measurement device 1, information relating to a correction part and serving as information representing a correction part where correction is performed, a type of a force to be corrected by the force correction unit 41, the constant "k" to correct the force in the force correction unit 41, and a correcting method used to correct a force in the force correction unit 41 are determined. In the force correction determination unit 36, the constant "k" is determined such that differences of flexibilities of the flexible substrate 45 are calculated in units of directions. The correcting method determined by the force correction determination unit 36 is output from the force correction determination unit 36 to the force correction unit 41 together with the information of the force.

Next, in step S206, based on the correcting method determined by the force correction determination unit 36, the force correction unit 41 corrects the force. The force correction unit 41 outputs the corrected information to the slave control unit 35 through the force correction determination unit 36. When the force correction determination unit 36 determines "no correction" at the force correction part, the force correction unit 41 directly outputs the force detected by the force measurement device 1 to the slave control unit 35 through the force correction determination unit 36 without causing the force correction unit 41 to correct the force detected by the force measurement device 1.

Next, in step S207, the force information output from the force correction unit 41 to the slave control unit 35 is sent from the slave control unit 35 to the master control unit 28 and transmitted to the force transmitting unit 27. The force information input to the force transmitting unit 27 is transmitted to a hand of the worker 49.

Effects of Second Embodiment

As described above, in the second embodiment, when a flexible substrate insertion task is performed by using the master-slave device 100B, even though the slave mechanism 40 of the slave robot 26B and the master mechanism 33 of the master robot 25 have different inertia forces, the force correction determination unit 36 determines a correcting method for the force information to correct the force information in the force correction unit 41, and the master control unit 28 and the slave control unit 35 control the master-slave robot based on the corrected force information. Furthermore, when the master-slave robot is controlled as described above, a slave operation can be stopped when an overload is applied to the flexible substrate 45 or the insertion hole 46 while the master robot 25 is taught by the slave operation generating unit 51, or an operation to automatically operate the slave robot 26B can be generated after the master robot 25 is taught to make it possible to cause the slave control unit 35 to automatically operate the slave robot 26B. In a force correction state, a fluctuation of a position can also be smoothed by the slave operation generating unit 51 to make it possible to correct the operation. As a result, the master mechanism 33 can be prevented from being largely moved due to application of large force to the master mechanism 33, and the worker 49 can feel the fed-back force even though the correction is performed to prevent the master mechanism 33 from being largely moved.

Third Embodiment

In a third embodiment, as in the second embodiment, as shown in FIG. 15, an example, a description will be given of a case in which an inserting task of the flexible substrate 45 is performed by using a master-slave device (master-slave robot) 100C. A portion obtained by removing the slave mechanism 40 and the master mechanism 33 from the master-slave device 100C is also called a control apparatus for a master-slave robot.

Figure 20:
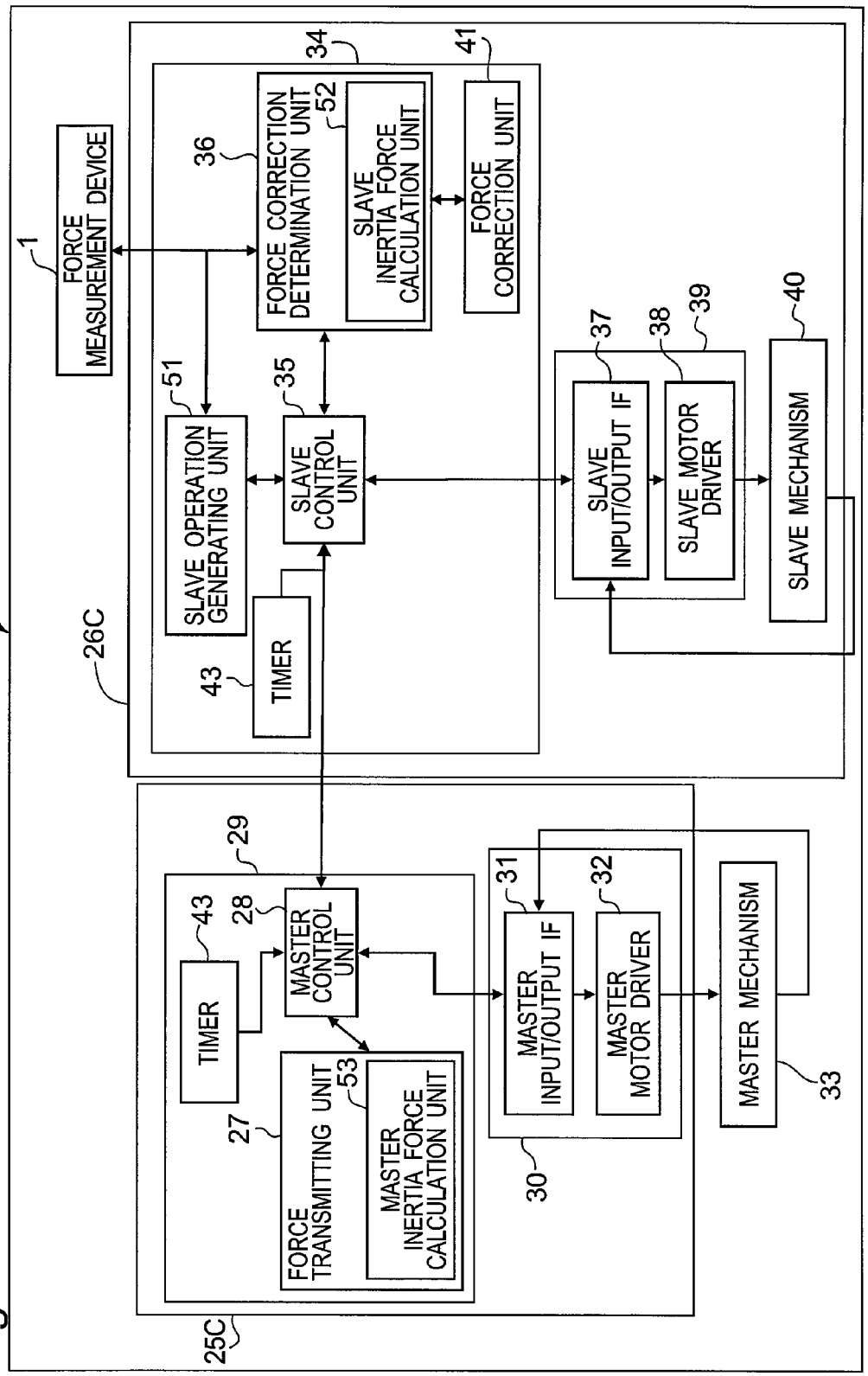
FIG. 20 is a block diagram showing a detailed configuration of a master-slave device according to a third embodiment of the present invention.

FIG. 20 shows configurations of the force measurement device 1, the master robot 25C, the slave robot 26C in the third embodiment. The descriptions of the portions common in the second and third embodiments are omitted, and only different portions will be described below.

<<Force Correction Determination Unit 36>>

The force correction determination unit 36 determines information relating to a force correcting method based on the force information input from the force measurement device 1 to the force correction determination unit 36 and outputs information relating to the determined force correcting method together with the force information from the force correction determination unit 36 to the slave control unit 35. More specifically, the force correction determination unit 36 determines, out of the force information detected by the force measurement device 1, information relating to a correction part serving as information representing a specific force detection part to be corrected, a type of a force corrected by the force correction unit 41, and a correcting method in the force correction unit 41 (will be described later), as information relating to a force correcting method.

Firstly, a type of a force to be corrected by the force correction unit 41 is determined by the force correction determination unit 36. The type is determined by the force correction determination unit 36 using the same method as that in the first embodiment.

Secondly, an inertia force of the slave mechanism 40 of a slave robot 26C to correct a force in the force correction unit 41 is calculated by a slave inertia force calculation unit 52 in the force correction determination unit 36.

The force correction determination unit 36, as in the first embodiment, includes a force correction determination main unit that determines a force type or the like and the slave inertia force calculation unit 52 that calculates an inertia force of the slave mechanism 40 as will be described later.

In this case, the slave inertia force calculation unit 52 is included in the force correction determination unit 36 and calculates an inertia force (m×a) of the slave mechanism 40 based on an acceleration "a" and a weight "m" of the slave mechanism 40 of the slave robot 26C. A value obtained by subtracting the inertia force of the slave mechanism 40 calculated by the slave inertia force calculation unit 52 from the force information measured by the force measurement device 1 is calculated by the slave inertia force calculation unit 52 as a force fed back to the master robot 25. Correction of an actual force is performed by the force correction unit 41 (will be described later) based on the information from the slave inertia force calculation unit 52. As the weight "m", a weight of the slave mechanism 40 is determined in advance. The acceleration "a" of the slave mechanism 40 of the slave robot 26C is calculated such that the velocity of the slave mechanism 40 of the slave robot 26C is differentiated by the slave inertia force calculation unit 52. As the velocity and the acceleration of the slave mechanism 40, a velocity is calculated by differentiating a position (tip end position of the slave robot 26B) detected by the instrument position detection unit 19, and an acceleration is calculated by differentiating the velocity.

<<Force Correction Unit 41>>

The force correction unit 41, as in the first embodiment, corrects a force that should be transmitted to the master mechanism 33 by the force transmitting unit 27 according to the correction part and a correcting method that are determined by the force correction determination unit 36.

More specifically, when the force correction determination unit 36 determines "no correction" at the force correction part, the force correction unit 41 outputs the force detected by the force measurement device 1 to the slave control unit 35 through the force correction determination unit 36 without correcting the force.

When the force correction determination unit 36 determines "correction" at the force correction part, the force correction unit 41 calculates a value obtained by subtracting the inertia force of the slave mechanism 40 calculated by the slave inertia force calculation unit 52 from the force information measured by the force measurement device 1, as a force fed back to the master robot 25.

<<Force Transmitting Unit 27>>

The force transmitting unit 27 transmits the information of the force corrected by a correction unit 41 to the worker 49 according to the master mechanism 33. More specifically, the force transmitting unit 27 force-controls the slave mechanism 40 through the slave control unit 35 based on a force obtained by adding an inertia force of the master calculated by a master inertia force calculation unit 53 to the force information from the slave control unit 35, so that the information is transmitted to a hand of the worker 49.

The force transmitting unit 27, as in the first embodiment, includes a force transmitting main unit that performs force transmission and the master inertia force calculation unit 53 that calculates an inertia force of the master mechanism 33 (as will be described below).

The master inertia force calculation unit 53 calculates the inertia force (m×a) of the master mechanism 33 based on the acceleration "a" and the weight "m" of the master mechanism 33 of the master robot 25C. A value obtained by adding an inertia force of the master mechanism 33 calculated by the master inertia force calculation unit 53 to the force information from the slave control unit 35 is calculated by the master inertia force calculation unit 53, and the master mechanism 33 is force-controlled by the master control unit 28 based on the calculated information to transmit the information to the hand of the worker 49. As the weight "m", a weight of the master mechanism 33 is determined in advance. The acceleration "a" of the master mechanism 33 of the master robot 25C is calculated such that a velocity of the master mechanism 33 of the master robot 25C is differentiated by the master inertia force calculation unit 53. The velocity of the master mechanism 33 is obtained by differentiating position information output from the master input/output IF 31.

Effects of Third Embodiment

As described above, even though the slave mechanism 40 of the slave robot 26C and the mechanism 33 of the master robot 25C have different inertia forces, the force correction determination unit 36 determines a correcting method for the force information to correct the force information in the force correction unit 41, and the master control unit 28 and the slave control unit 35 control the master-slave robot based on the corrected force information. In the correction of force information in the force correction unit 41, a force fed back to the master robot 25C is calculated by the force correction unit 41 based on the inertia force of the slave mechanism 40 calculated by the slave inertia force calculation unit 52 in the force correction determination unit 36. Based on the fed-back force and the inertia force of the master mechanism 33 calculated by the master inertia force calculation unit 53, the master control unit 28 force-controls the master mechanism 33 to transmit force information to a hand of the worker 49. As a result, the master mechanism 33 can be prevented from being largely moved due to application of large force to the master mechanism 33, and the worker 49 can feel the fed-back force when the correction is performed to prevent the master mechanism 33 from being largely moved. Furthermore, as far as the weights of the master mechanism 33 or the slave mechanism 40 are determined in advance, the inertia force is automatically calculated to make it possible to feed back a more accurate force to the worker 49.

<<Modification>>

Figure 9D:
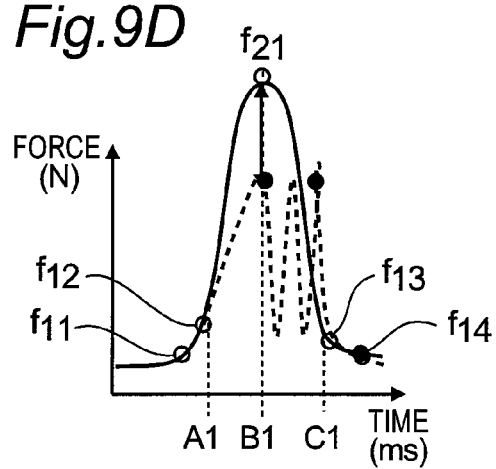
FIG. 9D is a graph showing a time-series change of a force in a second embodiment of the present invention.

The correction is performed by extending the force at the time point $t_{B1}$ from the time point $t_{B1}$ to the time point $t_{C1}$ in FIG. 9B in the first embodiment. However, as shown in FIG. 9D, correction may be performed by a third method in which the force at the time point $t_{B1}$ and the force at the time point $t_{C1}$ are alternatively switched every predetermined period of time and presented in a section from the time point $t_{B1}$ to the time point $t_{C1}$ as shown in FIG. 9D (in other words, correction is performed such that the force is repeatedly reduced and increased within a range that is not more than a value obtained by reducing an absolute value of force information at a force correction part by a predetermined correction amount). In this manner, when the strength and weakness of force are added, an advantage that causes the worker to more easily feel a presented force is obtained ("method C").

Figure 9E:
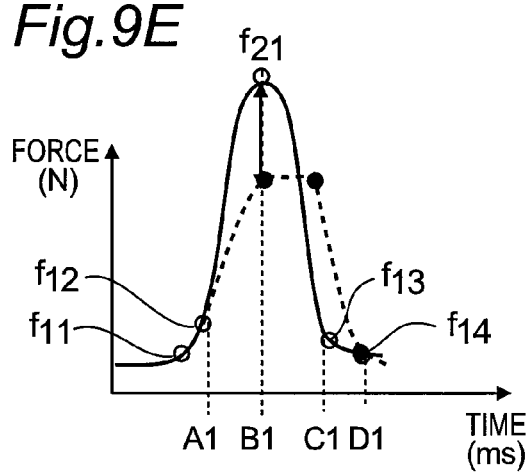
FIG. 9E is a graph showing a time-series change of a force in the second embodiment of the present invention.

The correction is performed by extending the force at the time point $t_{B1}$ from the time point $t_{B1}$ to the time point $t_{C1}$ in FIG. 9B in the first embodiment. However, as shown in FIG. 9E, correction may be performed by the force correction unit 41 such that, in order to prevent the force from being sharply reduced at the time point $t_{C1}$ and from transmitted, a section until a time point $t_{D1}$ serving as the next basing point is smoothly interpolated to prevent the force from being sharply reduced ("method D").

Figure 9F:
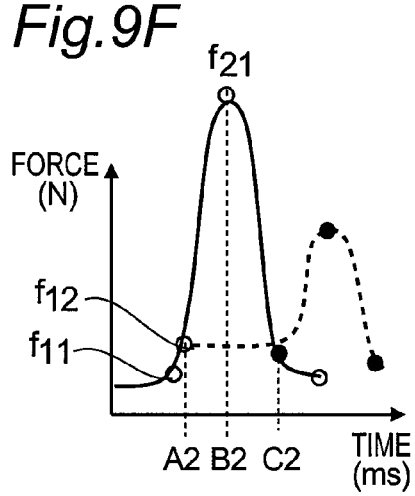
FIG. 9F is a graph showing a time-series change of a force in the second embodiment of the present invention.

As shown in FIG. 9F, when a peak represented by force information $f_{21}$ is detected when a period of time from a time point A2 to a time point C2 in FIG. 9F is within a predetermined period of time, a method of intentionally delaying a feedback timing by the force correction unit 41 may be used (method E). In this case, the predetermined period of time is, for example, a time from the start to the end of the peak (A2 to C2 in FIG. 9F). More specifically, the force correction determination unit 36 may use, in addition to the first to third methods, a fourth method that performs correction to reduce an absolute value of force information at a force correction part by a predetermined correction amount, after a predetermined period of time has elapsed, in the force correction unit 41. In this manner, a period of time in which a force is not fed back before the force is fed back or a period of time in which a force to be fed back is weakened is elongated to make it possible to feed back the force to the worker 49 such that the worker 49 more easily feels the force.

One of the correcting method according to the second embodiment and the correcting method of the modification is determined by the force correction determination unit 36 in advance, or determined by the force correction determination unit 36 based on the value of the constant "k". For example, when the constant "k" is smaller than the threshold value for determining a predetermined first correcting method (for example, less than 0.2), the "method A" is selected as the method. When the constant "k" is equal to or larger than the threshold value for determining the first correcting method and less than the threshold value for determining a second correcting method (for example, 0.2 or more and less than 0.4), the method is selected as a "method B" or a "method D". Furthermore, when the constant "k" is equal to or larger than the threshold value for determining the second correcting method, the method may be selected as a "method E".

Furthermore, in the embodiment, only the insertion direction is described. However, with respect to directions perpendicular to the insertion direction, measurement can be performed through the same method as described above.

In the second embodiment, the teaching of the task that attaches the flexible substrate 45 to the insertion hole 46 of the printed board 47 is described as an example. However, the present invention is effective in a task other than the teaching, such as a task that removes a defective minute component or incorporates a component.

Each of the threshold values is selected by the operator 6 or the worker 49 as values changing depending on types or states of an object or an object to be treated from a plurality of threshold values created in advance, for example. Alternatively, the operator or the worker 49 can also arbitrarily input the thresholds to the reference information generating unit 15, the force decision unit 12, the individual force calculation unit 11, the force correction determination unit 36, or the like by an input device such as a keyboard or a button through the database input/output unit 14.

Though the present disclosure has been described above based on the above first to third embodiments, the present disclosure should not be limited to the above-described first to third embodiments. For example, the present disclosure also includes the following cases.

Part or entirety of each of the above-described control apparatuses is actually a computer system that includes, for example, a microprocessor, ROM, RAM, hard disk unit, display unit, keyboard, mouse, and the like. A computer program is stored on the RAM or the hard disk unit. Functions of each of the units can be achieved by the microprocessor operating according to the computer program. The computer program mentioned here is a combination of a plurality of instruction codes that indicate commands to a computer for achieving predetermined functions.

For example, each component can be implemented as a result that a program executing section (part/unit) such as a CPU reads and executes software programs recorded in a recording medium such as a hard disk or semiconductor memory. Here, software that implements a part or entirety of the control apparatus according to each of the above-mentioned embodiments or modifications is a following program. That is to say, this program has a computer execute the sections (parts/units) defined in claims. The program has a computer execute the units/steps defined in claims. That is, such a program is a control program for a master-slave robot that controls a master-slave device comprising a slave mechanism that grips an object and performs a task while being in contact with an object to be treated and a master mechanism that causes a person to remotely-manipulate the slave mechanism, the control program causing a computer to execute the steps of:

causing a force information acquiring unit to acquire force information of an external force acting on the slave mechanism;

causing a force correction determination unit, based on at least one piece of information of the force information and velocity information of the slave mechanism, to determine a force correction part serving as information of a section from a correction start time serving as start time of correction of the force information to a correction end time serving as end time of the correction and, as a correcting method, any one of two methods including a first method that determines a gain such that a reduction in an absolute value of the force information of the force correction part at the force correction part is maintained for a predetermined period of time to perform correction and a second method that determines a gain such that a reduction and an increase in the absolute value of the force information of the force correction part at the force correction part are repeated within a range that is not more than a value obtained by reducing the absolute value, to perform correction;

causing a force correction unit to correct the force information acquired by the force information acquiring unit by the correcting method determined by the force correction determination unit based on the correction part and the gain that are determined by the force correction determination unit;

causing a force transmitting unit to transmit, to the master mechanism, force information after the correction is performed by the force correction unit;

causing a master control unit to control manipulation information of the master mechanism when the person manipulates a master manipulator based on the corrected force information transmitted from the force transmitting unit; and causing a slave control unit that is connected to the slave mechanism and the master control unit to output a control signal that transmits manipulation information of the master mechanism sent from the master control unit to the slave mechanism.

In addition, it may be possible to execute the program by downloading it from a server or the like or reading it from a predetermined storage medium (an optical disc such as a CD-ROM, a magnetic disc, a semiconductor memory, or the like).

Further, one or more computers can be used to execute the program. That is, centralized processing or distributed processing can be performed.

By properly combining the arbitrary embodiment(s) or modification(s) of the aforementioned various embodiments and modifications, the effects possessed by the embodiment(s) or modification(s) can be produced.

The present invention is useful as a control apparatus and method for a master-slave robot, a master-slave robot, and a control program, each of which grips an object and performs a task while being in contact with an object to be treated.

The entire disclosure of Japanese Patent Application No. 2013-002687 filed on Jan. 10, 2013, including specification, claims, drawings, and summary are incorporated herein by reference in its entirety.

Although the present disclosure has been fully described in connection with the embodiments thereof with reference to the accompanying drawings, it is to be noted that various changes and modifications are apparent to those skilled in the art. Such changes and modifications are to be understood as included within the scope of the present disclosure defined by the appended claims unless they depart therefrom.

What is claimed is:

1. A control apparatus for a master-slave robot comprising a slave mechanism that grips an object and performs a task while being in contact with an object to be treated and a master mechanism that allows a person to remotely-manipulate the slave mechanism, the control apparatus comprising:
a force information acquiring unit that acquires force information of an external force acting on the slave mechanism;
a force correction determination unit that, based on at least one piece of information of the force information and velocity information of the slave mechanism, determines a force correction part and a correcting method;
a force correction unit that corrects the force information acquired by the force information acquiring unit by the correcting method determined by the force correction determination unit based on the force correction part and the correcting method that are determined by the force correction determination unit;
a force transmitting unit that transmits, to the master mechanism, corrected force information after the correction is performed by the force correction unit;
a master control unit that controls manipulation information of the master mechanism when the master mechanism is manipulated based on the corrected force information transmitted from the force transmitting unit; and
a slave control unit that is connected to the slave mechanism and the master control unit and outputs a control signal that transmits the manipulation information of the master mechanism sent from the master control unit to the slave mechanism,
wherein the force correction determination unit determines the force correction part serving as information of a section from a correction start time serving as a start time of correction of the force information to a correction end time serving as an end time of the correction, based on the at least one piece of information of the force information and the velocity information of the slave mechanism, and
wherein the force correction determination unit determines at the determined force correction part, the correction method in which correction is performed by repeatedly reducing and increasing the force within a range that is not more than a value obtained by reducing an absolute value of the force information at the force correction part by a predetermined correction amount.

2. The control apparatus for a master-slave robot according to claim 1, wherein
the force information acquiring unit includes:
a force detection unit that detects information of the force obtained when the object is brought into contact with the object to be treated;
a reference information generating unit that generates reference information serving as information relating to a force in the object being not in contact with the object to be treated; and
an individual force calculating unit that individually calculates a force generated when the object acts on the object to be treated based on the information of the force acquired by the force detection unit and the reference information when the object is brought into contact with the object to be treated, and
the force correction determination unit determines the force correction part and determines whether a force to be corrected by the force correction unit is of a type of the information of the force acquired by the force information acquiring unit or a type of the force individually acting on the object to be treated by the object.

3. The control apparatus for a master-slave robot according to claim 1, wherein
the force correction determination unit determines a correction amount set when the absolute value of the force information at the force correction part is reduced, based on at least one piece of information of a type of one of the force acquired by the force information acquiring unit and the force individually acting on the object to be treated by the object and information of a degree of flexibility of the object or the object to be treated.

4. The control apparatus for a master-slave robot according to claim 3, wherein
the force correction determination unit determines a correction amount such that the correction amount decreases with an increased degree of flexibility of the object or the object to be treated in a plurality of directions including a task direction and a direction intersecting with the task direction.

5. The control apparatus for a master-slave robot according to claim 3, wherein
the force correction determination unit determines correction such that a correction amount set when the type of the force determined by the force correction determination unit is determined as the force individually acting on the object to be treated by the object is larger than a correction amount determined as the information of the force acquired by the force information acquiring unit.

6. The control apparatus for a master-slave robot according to claim 2, further comprising
a force decision unit that decides that a load is applied to the object or the object to be treated, when the information of the force detected by the force detection unit or the individual force calculated by the individual force calculating unit is not less than a predetermined threshold value for deciding load.

7. The control apparatus for a master-slave robot according to claim 6, further comprising
a decision result notification unit that adds the force calculated by the reference information generating unit or the individual force calculated by the individual force calculating unit or a decision result decided by the force decision unit to an image obtained by imaging the object or the object to be treated to display a resultant image.

8. The control apparatus for a master-slave robot according to claim 6, further comprising
a decision result notification unit that provides a notification, by voice, of the force calculated by the reference information generating unit or the individual force calculated by the individual force calculating unit or a decision result decided by the force decision unit.

9. A method of controlling a master-slave robot that controls a master-slave device comprising a slave mechanism that grips an object and performs a task while being in contact with an object to be treated and a master mechanism that allows a person to remotely-manipulate the slave mechanism, the method comprising:

causing a force information acquiring unit to acquire force information of an external force acting on the slave mechanism;

causing a force correction determination unit, based on at least one piece of information of the force information and velocity information of the slave mechanism, to determine a force correction part and a correcting method;

causing a force correction unit to correct the force information acquired by the force information acquiring unit by the correcting method determined by the force correction determination unit based on the force correction part and the correcting method that are determined by the force correction determination unit;

causing a force transmitting unit to transmit, to the master mechanism, corrected force information after the correction is performed by the force correction unit;

causing a master control unit to control manipulation information of the master mechanism when the master mechanism is manipulated based on the corrected force information transmitted from the force transmitting unit; and causing a slave control unit that is connected to the slave mechanism and the master control unit to output a control signal that transmits the manipulation information of the master mechanism sent from the master control unit to the slave mechanism, wherein when the force correction determination unit determines the force correction part and the correcting method, the force correction determination unit determines the force correction part serving as information of a section from a correction start time serving as a start time of correction of the force information to a correction end time serving as an end time of the correction, based on the at least one piece of information of the force information and the velocity information of the slave mechanism, and wherein the force correction determination unit determines at the determined force correction part, the correction method in which correction is performed by repeatedly reducing and increasing the force within a range that is not more than a value obtained by reducing an absolute value of the force information at the force correction part by a predetermined correction amount.

10. A non-transitory computer-readable recording medium including a control program for a master-slave robot that controls a master-slave device comprising a slave mechanism that grips an object and performs a task while being in contact with an object to be treated and a master mechanism that allows a person to remotely-manipulate the slave mechanism, the control program causing a computer to execute the steps of:

causing a force information acquiring unit to acquire force information of an external force acting on the slave mechanism;

causing a force correction determination unit, based on at least one piece of information of the force information and velocity information of the slave mechanism, to determine a force correction part and a correcting method;

causing a force correction unit to correct the force information acquired by the force information acquiring unit by the correcting method determined by the force correction determination unit based on the force correction part and the correcting method that are determined by the force correction determination unit;

causing a force transmitting unit to transmit, to the master mechanism, corrected force information after the correction is performed by the force correction unit;

causing a master control unit to control manipulation information of the master mechanism when the master mechanism is manipulated based on the corrected force information transmitted from the force transmitting unit; and causing a slave control unit that is connected to the slave mechanism and the master control unit to output a control signal that transmits manipulation information of the master mechanism sent from the master control unit to the slave mechanism, wherein in the step of determining the force correction part and the correcting method:

the force correction determination unit determines the force correction part serving as information of a section from a correction start time serving as a start time of correction of the force information to a correction end time serving as an end time of the correction, based on the at least one piece of information of the force information and the velocity information of the slave mechanism, and the force correction determination unit determines at the determined force correction part, the correction method in which correction is performed by repeatedly reducing and increasing the force within a range that is not more than a value obtained by reducing an absolute value of the force information at the force correction part by a predetermined correction amount.

* * * * *